United States Patent [19]

Woroniecki et al.

[11] Patent Number: 4,795,809

[45] Date of Patent: Jan. 3, 1989

[54] NOVEL CLAVAM DERIVATIVES AND METHODS OF MAKING SAME

[75] Inventors: Stefan R. Woroniecki; Stephen W. Elson; Keith H. Baggaley, all of Betchworth, England

[73] Assignee: Beecham Group plc, Middlesex, England

[21] Appl. No.: 900,744

[22] Filed: Aug. 27, 1986

[30] Foreign Application Priority Data

Aug. 29, 1985 [GB] United Kingdom ................ 8521516

[51] Int. Cl.⁴ ................ C07D 498/04; C07D 205/08; C12P 17/18; C12P 1/465
[52] U.S. Cl. ................................... 540/348; 435/119; 540/362
[58] Field of Search ........................ 540/348

[56] References Cited

U.S. PATENT DOCUMENTS 4,078,067 3/1978 Christenser ........................ 514/210

FOREIGN PATENT DOCUMENTS 2747599 4/1978 Fed. Rep. of Germany ...... 544/348
1585124 2/1981 United Kingdom .
1603208 11/1981 United Kingdom .

OTHER PUBLICATIONS

Ivanitskaya, Chem. Abs. 103, 213286e.
Muller, J. Antibiotics 36, 217.
"Protecting Groups", Green et al., Chapters 5 and 7.
"Biochemistry", 2nd edition, Lehniger, pp. 886-887 and 118-119.

Primary Examiner—Mark L. Berch
Attorney, Agent, or Firm—Hopgood, Calimafde, Kalil, Blaustein & Judlowe

[57] ABSTRACT

A compound having the formula (I):

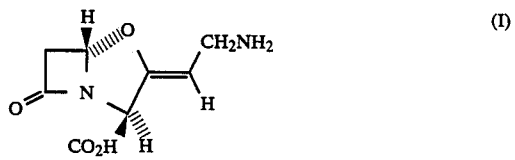

is described, together with salts thereof and an enzymatic process for converting such compounds into clavulanic acid.

A process for the preparation of the compound of formula (I) and its salts is disclosed, together with intermediates for use therein.

2 Claims, No Drawings

NOVEL CLAVAM DERIVATIVES AND METHODS OF MAKING SAME

This invention relates to B-lactam compounds and in particular to a novel clavam derivative. This invention also relates to a process for the preparation of clavam derivatives.

British Patent Specification No. 1 508 977 describes a clavam derivative known as clavulanic acid, which is a compound produced by *Streptomyces clavuligerus* ATCC 27064 or a high yielding mutant thereof. Clavulanic acid has the structure (A) shown hereinbelow in which the absolute stereochemistry and a system of numbering are also indicated.

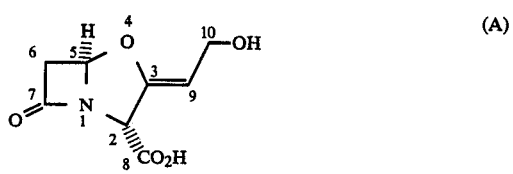

Clavulanic acid is thus Z-(2R,5R)-3-(β-hydroxyethylidene)-7-oxo-4-oxa-1-azabicyclo[3.2.0]heptane-2-carboxylic acid.

Clavulanic acid is a potent inhibitor of β-lactamase enzymes and is a compound of great clinical value since it protects β-lactamase-labile β-lactam antibiotics from degradation.

The present invention provides a compound of formula (I) or a salt or protected form thereof:

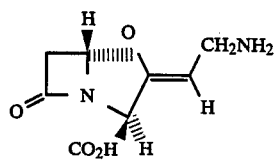

In formula (I), which is numbered in the same way as clavulanic acid, the absolute stereochemistry at the 2- and 5- positions is opposite to that in clavulanic acid, i.e. is 2S,5S. Hence the compound of formula (I) and its salts and esters show a negative Cotton effect in the CD (Circular Dichroism) spectrum in the region of 230–240 nm in contrast to the positive inflection shown by clavulanic acid in the same region.

The utility of the compound of formula (I) and its salts resides in their ability to act as intermediates in a process for preparing clavulanic acid as hereinbelow described.

The compound of formula (I) may be in the zwitterionic form or in salt form, for example as a metal salt such as, for example, the sodium salt, an acid addition salt, an ammonium salt or a substituted ammonium salt, for example a tertiary amine salt.

Acid addition salts may form at the terminal amino group and may be, for example, salts with inorganic acids such as, for example, hydrochloric acid, hydrobromic acid, orthophosphoric acid or sulphuric acid, or organic acids such as, for example, methanesulphonic acid, toluenesulphonic acid, acetic acid, propionic acid, lactic acid, citric acid, fumaric acid, malic acid, succinic acid, salicylic acid or acetylsalicylic acid.

Metal salts may form at the carboxyl group and may be, for example, aluminium salts and alkali metal and alkaline earth metal salts, such as, for example, lithium, sodium, potassium, calcium and magnesium salts.

Substituted ammonium salts may be, for example, those with $C_{1-6}$ alkylamines such as, for example, triethylamine, hydroxy($C_{1-6}$) alkylamines such as, for example, 2-hydroxyethylamine, bis(2-hydroxyethyl)amine or tri(2-hydroxyethyl)amine, cycloalkylamines such as, for example, bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as, for example, pyridine, collidine or quinoline.

It is to be understood that the present invention extends to a compound of formula (I) in which one or more of the functional groups present are in protected form. Thus the carboxy group may be protected, the amino group may be protected or both the carboxy and the amino group may be protected. All such protected forms of the compound of formula (I) and other compounds herein described are embraced by the term 'protected form'. In addition, the term 'protected form' as applied to compounds herein described covers 'masked' intermediates, which may be converted into the final compounds by chemical processes known to be capable of converting one functional group into another (wherein the remainder of the molecule remains substantially unaffected). For example, preferred masked forms of an amine include the corresponding azido and cyano analogues which may be converted into the desired amine by reduction. (It will be appreciated that the corresponding cyano compound has one less carbon atom in the side-chain, excluding the carbon in the cyano group.)

Suitable ester forming carboxyl-protecting groups include optionally substituted $C_{1-6}$ alkyl, $C_{2-6}$ alkenyl, $C_{2-6}$ alkynyl, $C_{3-7}$ cycloalkyl, aryl, aryl $C_{1-6}$ alkyl, and tri $C_{1-6}$ alkylsilyl groups.

When used herein the term "aryl" includes phenyl and naphthyl, each optionally substituted with up to five fluorine, chlorine, $C_{1-6}$ alkyl, $C_{1-6}$ alkoxy, halo ($C_{1-6}$)alkyl, hydroxy, amino, carboxy, $C_{1-6}$ alkoxycarbonyl, aryloxycarbonyl, $C_{1-6}$ alkoxycarbonyl($C_{1-6}$)alkyl, nitro, aryloxycarbonyloxy, aryl $C_{1-6}$ alkyloxycarbonyloxy, $C_{1-6}$ alkyloxycarbonyloxy, $C_{1-6}$ alkylcarbonyloxy, arylcarbonyloxy, aryl $C_{1-6}$ alkylcarbonyloxy, or aryl $C_{1-6}$ alkyloxycarbonyl groups.

The term "halogen" refers to fluorine, chlorine, bromine and iodine. The terms halo and halide should be interpreted accordingly.

Some examples of optional substituents in protecting groups mentioned herein as being optionally substituted include up to three groups (which may be the same or different) chosen from halogen, hydroxy, $C_{1-6}$ alkoxy, $C_{1-6}$ alkylthio, cyano, nitro, carboxy, carboxylic acid $C_{1-6}$ alkyl ester, carbamoyl, amino, mono ($C_{1-6}$) alkylamino, and di ($C_{1-6}$) alkylamino.

Particularly suitable ester-forming carboxyl-protecting groups are those which may be removed under conventional conditions. Such groups include $C_{1-6}$ alkyl such as methyl and ethyl, benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, or a silyl, stannyl or phosphoruscontaining group.

A carboxyl group may be regenerated from any of the above esters by usual methods appropriate to the particular ester group, for example, acid- and base-catalysed hydrolysis, or by enzymically-catalysed hydrolysis, or by hydrogenolysis under conditions wherein the remainder of the molecule is substantially unaffected.

A preferred carboxyl protecting group in the compound of formula (I) or a salt or amino-protected derivative thereof is benzyl.

Suitable protecting groups for the amino group are those which may readily be cleaved. A comprehensive discussion of the ways in which an amino group may be protected and methods for cleaving the resulting protected derivatives are given, for example, in "Protective Groups in Organic Synthesis" by T. W. Greene (Wiley-Interscience, New York, 1981).

Suitable examples of amino protecting groups include masking groups as hereinabove discussed; optionally substituted $C_{1-6}$ alkylcarbonyl; arylcarbonyl; aryl $C_{1-6}$ alkylcarbonyl; (heterocyclyl)carbonyl wherein the heterocyclyl group is a 5- or 6- membered aromatic ring containing up to 4 heteroatoms selected from oxygen, nitrogen and sulphur; or a group affording a carbamate such as benzyloxycarbonyl optionally substituted in the phenyl ring by one or two substituents selected from $C_{1-4}$ alkyl, $C_{1-4}$ alkoxy, trifluoromethyl, halogen or nitro; $C_{1-4}$ alkyloxycarbonyl, for example tert-butoxycarbonyl; or $C_{1-4}$ alkyloxycarbonyl optionally substituted in the alkyl group by up to three substituents chosen from $C_{1-4}$ alkoxy, halo or nitro, for example 2,2,2,-trichloroethoxycarbonyl or 1-chloroethoxycarbonyl.

Preferred examples of N-protecting groups for the amino group present in compound (I) include those conventionally known for amino protection in peptide chemistry, as discussed hereinbelow.

A particularly preferred amino protecting group in the compound of formula (I) or a salt or carboxy-protected derivative thereof is benzyloxycarbonyl.

Desirably the compound of formula (I) will be in isolated form, free of nucleic acid material. The compound is suitably, for example, substantially pure, more suitably at least 75% pure and preferably at least 85% pure, for example, 90–100% pure. One preferred isolated form is as the solid form, more preferably as the crystalline form. However, it should be understood that none of the above precludes using compound (I) in an impure form.

When the compounds of this invention are allowed to crystallise, or are recrystallised, from organic solvents, solvent of crystallisation may be present in the crystalline product. This invention includes within its scope such solvates. Similarly, the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Specific compounds within this invention of formula (I) or a salt or protected form thereof include the following:

Z-(2S,5S)-3-(β-aminoethylidene)-7-oxo-4-oxa-1-azabicyclo[3.2.0]heptane-2-carboxylic acid;

Z-(2S,5S)-3-(β-benzyloxycarbonylaminoethylidene)-7-oxo-4-oxa-1-azabicyclo[3.2.0]heptane-2-carboxylic acid; and benzyl Z-(2S,5S)-3-(β-benzyloxycarbonylaminoethylidene) -7-oxo-4-oxa-1-azabicyclo[3.2.0.]heptane-2-carboxylate.

The present invention also provides a process for the preparation of a compound of formula (I) or a salt or protected form thereof, which process comprises treating a precursor compound of formula (II) or a salt thereof:

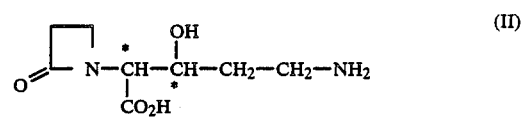

with an enzyme system capable of effecting the desired cyclisation, and thereafter, if necessary or desired, converting the product into a salt or protected form thereof.

The term 'enzyme system' as used herein denotes either one enzyme or a series of enzymes.

The present invention further provides a compound of formula (II) or a salt or protected form thereof.

Compounds of formula (II) have two asymmetric carbon atoms, marked with asterisks in the formula. These compounds may, therefore, exist in four stereoisomeric forms. The present invention encompasses all stereoisomers of the compounds of formula (II) and the use thereof whether free from other isomers or admixed with other isomers inany proportion, and thus includes, for instance, racemic mixtures of enantiomers. Solvates, especially hydrates, of the compound of formula (II) or a salt thereof are also included within the scope of the invention. The invention also extends to protected derivatives of the compound of formula (II), i.e. compounds in which one or more of the functional groups is in protected form.

Suitable protecting groups for the carboxyl and amino groups in the compound of formula (II) include those indicated hereinabove as suitable for protecting the carboxyl and amino groups in the compound of formula (I).

A preferred protecting group for the carboxyl group in compounds of formula (II) is benzyl.

Preferred protecting groups for the amino group in compounds of formula (II) include benzyloxycarbonyl and azido.

Suitable protecting groups for the hydroxy group in the compound of formula (II) include those discussed by T. W. Greene (loc. cit.). Particularly suitable protecting groups include those which afford esters, for example an optionally substituted $C_{1-6}$ alkanoyl ester such as the acetate; optionally substituted $C_{1-6}$ alkyl- and aryl-carbonates; optionally substituted $C_{1-6}$ alkyl-, aryl- and aryl $C_{1-6}$ alkyl ethers; optionally substituted tri- $C_{1-6}$ alkyl silyl ethers; and acetals (for example tetrahydropyranyloxy derivatives, sometimes described as 'THP ethers').

Desirably the compound of formula (II) will be in isolated form, free of nucleic acid material. The compound is suitably, for example, substantially pure, more suitably at least 75% pure and preferably at least 85% pure, for example, 90–100% pure. One preferred isolated form is as the solid form, more preferably as the crystalline form. However, it should be understood that none of the above precludes using compound (II) in an impure form.

The compound of formula (II) may be in the zwitterionic form.

The salts of compounds of formula (II) may be, for example, acid addition salts, metal salts, ammonium salts and substituted ammonium salts, for example tertiary amine salts. Salt formation is possible at either or both the carboxyl group and the terminal amino group. Examples of suitable salts include those mentioned above for salts of compound (I).

Particular compounds of the formula (II) or a salt or protected form thereof include the following:

5-amino-3-hydroxy-2-(2-oxoazetidin-1-yl)valeric acid;
5-benzyloxycarbonylamino-3-hydroxy-2-(2-oxo-azetidin-1-yl)valeric acid;
benzyl 5-benzyloxycarbonylamino-3-hydroxy-2(2-oxoazetidin-1-yl)valerate; and
benzyl 5-azido-3-hydroxy-2-(2-oxoazetidin-1-yl)-valerate.

The process of this invention is suitably carried out, for example, in a cell-free system, that is in the absence of living cells.

Preferably the enzyme system employed is derived from a microorganism, in particular a species of Streptomyces.

Alternatively, the enzyme(s) may be produced by genetic engineering.

If a cell-free system is employed, a cell-free extract is preferably produced by sonication or other disruption of the microorganisms, optionally thereafter removing cell debris, leaving the enzyme system in solution.

The enzyme sytem producing the compound of formula (I) or a salt thereof suitably comprises, for example, an oxygenase enzyme.

The oxygenase enzyme is suitably, for example, a dioxygenase of the type wherein one atom of the dioxygen molecule is transferred to each of two substrate molecules. The two substrate molecules may be the same or different. The precursor compound of formula (II) may serve as one substrate molecule and a molecule such as, for example, a 2-oxo-acid, such as 2-oxoglutaric acid, may serve as a second substrate (co-substrate) molecule. Those enzymes for which 2-oxoglutaric acid serves as co-substrate are preferred dioxygenases for use in the process of the present invention.

From the foregoing it will be appreciated that the oxygenase enzymes utilise molecular oxygen and accordingly, to facilitate reaction, the reaction medium should preferably be supplied with sufficient oxygen in order to maintain a suitable dissolved oxygen tension. Efficient transfer of oxygen from the gas phase into the solution phase is assisted by stirring or shaking of the reaction medium.

In addition to co-substrate and oxygen the oxygenase enzyme reaction mixture may contain one or more other cofactors. Usually those cofactors will include an additional source of ferrous ions, most suitably, for example, as ferrous sulphate.

A preferred source of the oxygenase enzyme is a species of Streptomyces such as, for example, strains of or derived from S.clavuligerus, S.jumonjinensis, S.katusurahamanus and S.lipmanii. In particular the following strains of these microorganisms are useful: S.clavuligerus ATCC 27064, S.jumonjinensis ATCC 29864, S.katsurahamanus T-272, IFO 13716 and FERM 3944 S.lipmanii NRRL 3584.

A preferred enzyme within the invention is derived from S.clavuligerus ATCC 27064 and shows the following characteristics:

(a) the ability to convert a compound of the formula (II) or a salt thereof as hereinabove defined into a compound of the formula (I) or a salt thereof as hereinabove defined;
(b) a single band corresponding to a molecular weight of approximately 48,000 daltons when examined by sodium dodecyl sulphate polyacrylamide gel electrophoresis;
(c) an isoelectric point (pI) of 5.65 when examined by isoelectric focusing.

The oxygenase enzyme may be prepared by culturing the microorganism in a conventional manner, especially under aerobic conditions in a suitable liquid or semi-solid medium. In general, carbon and nitrogen sources which microorganisms can assimilate and inorganic salt nutrients essential for the growth of the microorganisms are included in the culture medium. In view of the nature of the prosthetic groups in oxygenase enzymes the culture medium should contain a source of metal ions such as, for example, iron. The culture conditions may be a temperature in the range of from 10° C. to 80° C. and pH in the range of from 3 to 10. Preferred conditions are from 20° C. to 30° C. at a pH of from 5 to 9, suitably, for example, about pH 7, for 0.5 to 5 days.

The oxygenase enzyme may be isolated and used in purified form, partially purified form, as obtained in an impure state, as a filtrate from a disrupted cell preparation, or as a crude cell homogenate.

Most suitably the enzyme is, for example, at least partially purified to remove other enzymes which might catalyse the destruction of the precursor, the enzyme, or the clavam nucleus. The enzyme may be attached to an insoluble polymeric support.

The process of the present invention is generally carried out in aqueous media, the reaction mixture suitably being maintained in the range of from pH 4 to 9, more suitably, for example, from 6.5 to 8.5, preferably about pH 7.0 to 7.5. The pH is suitably controlled, for example, using buffers, such as, for example, 3-(N-morpholino)propanesulphonic acid buffer at pH 7. Alternatively the pH may be controlled by the addition of a suitable acid or base. The temperature of the reaction should be that suitable for the enzyme employed and is generally in the range of from 15° C. to 60° C., preferably about 30° C. The reaction time depends on such factors as concentrations of reactants and cofactors, temperature and pH.

The precursor (II) or salt thereof is suitably dissolved, for example, in buffer before mixing with the enzyme. The concentration of precursor solution will depend upon the solubility of the precursor; usually the concentration of the precursor solution is in the range of from 5% w/v to 0.001% w/v. After the reaction is complete, the enzyme may be separated from the reaction mixture and the compound of formula (I) or a salt thereof isolated by conventional methods. The initial purification of the compound of formula (I) or a salt thereof conveniently involves a chromatography step. The compound of formula (I) may be isolated in a form where the carboxyl and/or the amino group present is protected and, if desired, the protecting group(s) may be subsequently removed to generate compound (I) in a pure form.

Instead of employing a cell-free system, the process of this invention may also be operated using an intact microorganism. The precursor compound of formula (II) or salt thereof is then provided and contacted with the microorganism to produce the compound of formula (I) or salt thereof. The microorganism may be in the form of a growing culture, resting culture, washed mycelium, immobilised cells, or protoplasts.

A compound of formula (II) may be prepared by cyclisation of a compound of general formula (III):

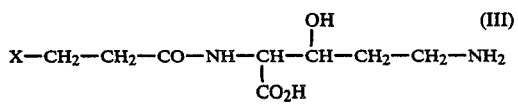

wherein X is a leaving group and the functional groups $CO_2H$, OH and $NH_2$ may be protected.

A leaving group represented by X is any group that will, under the reaction conditions, cleave from a starting material thus promoting reaction at a specified site. The group X herein may be hydroxyl or esterified hydroxyl such as a sulphate ester optionally substituted by halogen; halo, for example bromo, chloro or iodo; or aryl- or alkyl- sulphonyloxy such as, for example, p-toluenesulphonyloxy (tosyl) or methanesulphonyloxy (mesyl); or an alkyl oxonium salt.

The above process is preferably carried out under basic conditions, for example in the presence of sodium or potassium hydroxide, or sodium or potassium hydride.

The cyclisation reaction may be carried out:

(a) wherein X is halo, or aryl- or alkyl-sulphonyloxy, or an alkyl oxonium salt of the alcohol, in the presence of a solvent such as, for example, dimethylsulphoxide, dimethylformamide, hexamethylphosphoramide, dichloromethane, acetonitrile or ethyl acetate, or mixtures of any such solvents;

(b) wherein X is halo or a sulphate ester of the alcohol such as, for example, the chlorosulphate ester, by phase transfer catalysis methods in aqueous and/or organic solution in the presence of a quaternary ammonium salt such as tetrabutyl ammonium bisulphate or halid, or benzyltrimethyl ammonium halide;

(c) wherein X is hydroxyl in the presence of a suitable reagent, such as, for example, $(C_6H_5)_3P/C_2H_5O_2CN=NCO_2C_2H_5$.

Suitable examples of N-protecting groups for the amino group present in compound (III) include those conventionally known for this use in peptide chemistry. Examples of such groups include carboxylic acid groups such as, for example, acetyl, chloroacetyl, trifluoroacetyl, butyryl, benzoyl, phenylacetyl, pyridinecarbonyl; or an acid group derived from carbonic acid such as, for example, ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p-methoxyphenylazo)benzyloxycarbonyl, t-amyloxycarbonyl; or an acid group derived from a sulphonic or p-toluenesulphonic acid; or other groups such as, for example, benzyl, trityl, formyl, phthaloyl, o-nitrophenylsulphenyl, benzylidene or nitro. Preferred N-protecting groups include t-butoxycarbonyl and benzyloxycarbonyl. In certain instances, the nitrogen atom may be substituted with two of the above groups, for example with benzyl and with benzyloxycarbonyl. Alternatively the amino group present may be protected in the form of an azido group or a cyano group, and may be generated by a suitable method, for example by reduction.

The removal of the protecting group(s) present in the resultant compound may be effected by an appropriate procedure depending upon the kind(s) of the protective group(s). Some typical procedures are as follows: hydrogenation in the presence of palladium catalyst (for example palladium carbon, palladium black) for benzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl and trityl groups protecting the terminal amino group; treatment with hydrogen bromide in glacial acetic acid for benzyloxycarbonyl, p-bromobenzyloxycarbonyl, p-phenylazobenzyloxycarbonyl, t-butoxycarbonyl groups protecting the terminal amino group; treatment with metallic sodium in liquid ammonia for benzyloxycarbonyl, p-bromobenzyloxycarbonyl and tosyl groups protecting the terminal amino group; treatment with hydrochloric acid and/or acetic acid for trityl, t-butoxycarbonyl, formyl and benzylidene groups protecting the terminal amino group. Alternatively, deprotection may be effected with a suitable hydrolytic enzyme, for example an amidase. A terminal azido or cyano group may be reduced to an amino group by, for example, hydrogenation in the presence of a palladium catalyst.

Suitable examples of carboxyl-blocking derivatives for the group $-CO_2H$ in compound (III) include salts and ester derivatives of the carboxylic acid. The derivative is preferably one which may readily be cleaved at a later stage of the reaction. Suitable examples of salts include metal salts, such as, for example, those with sodium, potassium and lithium, and tertiary amine salts, such as, for example, those with tri($C_{1-6}$)alkylamines, N-ethylpiperidine, 2,6-lutidine, pyridine, N-methylpyrrolidine, or dimethylpiperazine. A preferred salt is with triethylamine.

Suitable examples of ester-forming carboxyl-protecting groups in compound (III) are those which may be removed under conventional conditions, as indicated hereinabove as suitable for protecting the carboxyl group in compounds of formula (I) and (II).

The hydroxyl group may be protected in the same way as the hydroxy group in the compound of formula (II), for example in the form of a silyl ether, or as an ester derivative, in particular $C_{1-6}$ alkanoyl, for example as the acetate derivative.

The compounds of general formula (III), in which the functional groups present are free or one or more such groups are in protected form, are novel and form a further aspect of this invention.

The compound of general formula (III) may be prepared by coupling a compound of general formula (IV), or an N-acylating derivative thereof, with a compound of formula (V) or a derivative thereof which allows acylation to take place:

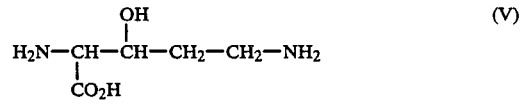

wherein X is as defined above and any functional groups may be protected.

The nature of the protecting groups and their removal is as discussed with respect to general formula (III) above. It may be convenient of course not to remove protecting groups from a protected form of compound (III), instead causing it to cyclise to give compound (II) in protected form as discussed hereinabove.

Suitable examples of groups which permit acylation to take place and which are optionally present on the α-amino group of the starting material of formula (V) include N-silyl, N-stannyl and N-phosphorus groups, for example trialkylsilyl groups such as trimethylsilyl, trialkyltin groups such as tri-n-butyltin, groups of formula —P·$R^aR^b$ wherein $R^a$ is an alkyl, aralkyl, alkoxy, haloalkyl, aryl, haloalkoxy, aryloxy, aralkyloxy or dialkylamino group, and $R^b$ is the same as $R^a$ or is halogen, or $R^a$ and $R^b$ together form a ring; suitable such phosphorus groups being, for example,

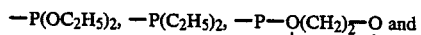

A reactive N-acylating derivative of the acid (IV) may be employed in the above process. The choice of reactive derivative will of course be influenced by the chemical nature of the substituents of the acid.

A suitable example of an N-acylating derivative is an acid halide, preferably the acid chloride or bromide. Acylation with an acid halide may be effected in the presence of an acid binding agent, for example a tertiary amine, such as, for example, triethylamine or dimethylaniline, an inorganic base, such as, for example, sodium hydroxide or sodium bicarbonate, or an oxirane, which binds hydrogen halide liberated in the acylation reaction. The oxirane is preferably a $(C_{1-6})$-1,2-alkylene oxide, such as, for example, ethylene oxide or propylene oxide. The acylation reaction using an acid halide may be carried out at a temperature in the range of from $-50°$ C. to $+50°$ C., in aqueous or non-aqueous media such as, for example, aqueous acetone, aqueous tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as, for example, methyl isobutyl ketone or butyl acetate.

Other suitable examples of N-acylating derivatives of the acid of general formula (IV) include activated esters, such as, for example, succinimido, phthalimido, p-nitrophenyl esters, or the anhydride of compound (IV) or mixed anhydrides of compound (IV) with other acids.

Alternatively, a compound of general formula (IV) may be coupled to a compound of formula (V) by using a dehydrating agent, suitably, for example, a carbodiimide reagent, such as, for example, N,N'-dicyclohexylcarbodiimide, or (1,3-dimethylaminopropyl)-3-ethylcarbodiimide.

The carbodiimide coupling reaction may be carried out in a water immiscible solvent, a water miscible solvent, a biphasic system or a mixture of water and water miscible solvent depending on the nature of the carbodiimide reagent and any protecting groups present in the compounds (IV) and (V).

Other coupling reagents which are used in peptide synthesis, such as, for example, dipyridyl disulphide/triphenylphosphine, are also suitable for preparation of compounds of general formula (III) from compounds (IV) and (V).

A compound of general formula (III) may also be prepared by reducing a compound of general formula (VI):

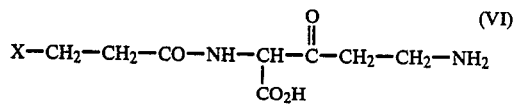

in which X is as defined above.

Suitably the reduction is carried out, for example, using a hydride reducing reagent, such as, for example, $NaBH_4$, $Zn(BH_4)_2$, or $NaBH_3CN$, in a suitable aqueous or organic solvent. Alternatively, compound (VI) may be reduced with a suitable enzyme in the presence of suitable co-factors, or reduced using whole cells such as yeast or liver cells.

A compound of general formula (VI) may be prepared by coupling a compound of general formula (IV) or an N-acylating derivative thereof with a compound of formula (VII):

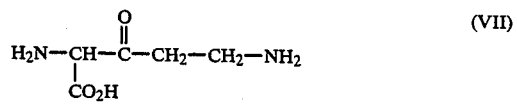

The carboxyl and δ-amino functions of compound (VII) may be suitably protected. Suitable examples of protection groups include those described above for protection of compounds of general formula (III). In addition, the carbonyl group in (VII) may be protected by methods known in the art, for example those described by T. W. Greene (loc.cit.). The methods described above for coupling a compound of general formula (IV) with a compound of formula (V) may be used for coupling a compound of general formula (IV) with a compound of formula (VII). Again it may be convenient not to remove any protecting groups present until the compound of general formula (III) is prepared, or indeed until after the compound of formula (III) in protected form has been cyclised.

A compound of the formula (VII) may be prepared by condensing a compound of formula (VIII) or general formula (IX) in which R is an ester-forming carboxyl-blocking group, with glycine (X)

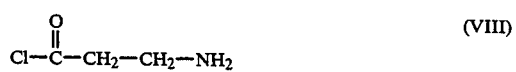

in the presence of, for example, a base in an anhydrous organic solvent.

Suitable examples of bases include inorganic bases such as, for example, sodium or potassium hydride, and organic bases such as, for example, lithium diisopropylamine, or lithium bis(trimethylsilyl)amide.

An ester-forming group R may be, for example, an alkyl or aralkyl group.

The amino and carboxyl functions of compounds (VIII), (IX) and (X) may be protected. If, during reaction with compound (IX), the carboxyl group of glycine (X) is protected by an ester-forming group, that group is preferably the same as the group R.

Suitable protecting groups include those described above for the compounds of general formula (III). For example, the amino functions of compounds (VIII) and (IX) may be protected as azido or cyano groups which may be subsequently converted to amino groups. In compound (X) the amino function may be protected as the N-(diphenylmethylene) or isonitrile derivative.

A compound of formula (V) may be prepared by a similar method, for example, by condensing a compound of formula (XI):

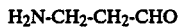  (XI)

H2N-CH2-CH2-CHO with glycine [formula (X)].

The carboxyl function of glycine (X) and the amino functions of glycine (X) and compound (XI) may suitably be protected by protecting groups hereinabove described.

The present invention also provides a process for the preparation of a compound of formula (II) or a salt or protected form thereof, which process comprises condensing a compound of formula (XIA):

Y-CH2CH2CHO  (XIA)

wherein Y is halo or amino, the amino group being optionally protected, with a compound of formula (XII) or a salt thereof:

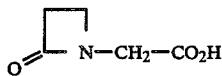  (XII)

wherein the carboxy group may be protected; and thereafter if necessary or desired carrying out one or more of the following steps:
  (i) converting the group Y into an amino group;
  (ii) converting the product into a free acid, salt, or protected form thereof.

Preferably the compound of formula (XIA) has the formula (XI) as hereinabove defined.

The condensation may be carried out using the basic conditions described above for the preparation of compound (VII). The carboxyl group of compound (XII) may be suitably protected and the amino group of compound (XI) may be protected. For example, the amino group may be protected as an azido group or a cyano group and may be generated by reduction.

In another preferred aspect, instead of compound (XI), it is possible to use as starting material the corresponding chloro compound of formula (XI'):

ClCH2CH2CHO  (XI')

The compound prepared on condensation with compound (XII) may be converted into a compound similar to compound (II), but having a terminal azido group, by reaction with a suitable azide, for example, sodium azide, in a suitable solvent, for example dimethyl sulphoxide. Compound (II) may then be generated by reduction of the terminal azido group.

In another aspect of the invention there is provided a process for the preparation of a compound of formula (II) or a salt or protected form thereof, which process comprises reducing a compound of formula (XIII) or a salt thereof:

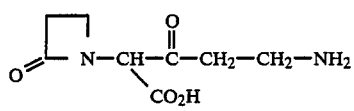  (XIII)

in which the carboxyl and amino functions may be protected, if desired, by the methods hereinabove described, and thereafter if necessary:
  (i) removing any protecting groups;
  (ii) converting the product into a free acid, salt, or protected form thereof.

Suitable examples of useful reducing agents are metal hydride complexes such as, for example, $NaBH_4$, $NaBH_3CN$, $Zn(BH_4)_2$, in aqueous or organic solvent media. Alternatively, compound (XIII) may be reduced with a suitable enzyme in the presence of suitable co-factors, or reduced using whole cells such as yeast or liver cells.

A compound of general formula (XIII) may be prepared from a compound of formula (VIII) or (IX) by condensation with a compound of formula (XII) using, for example, the basic conditions described above.

In a further route, a compound of formula (II) may be prepared by cyclisation of a compound of formula (XIV):

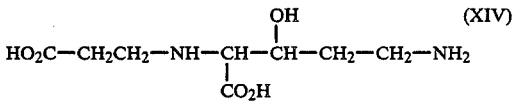  (XIV)

The functional groups in compound (XIV) may be protected as above. Suitable protecting groups include those described above for compounds of general formula (III). For the purposes of cyclisation, the carboxyl group of the propionyl moiety and the secondary amine function are preferably left unprotected. The cyclisation of compound (XIV) may be carried out by the use of a dehydrating agent. Agents commonly used for peptide synthesis are suitable. A carbodiimide reagent or a mixture of triphenylphosphine and dipyridyldisulphide may be used, for example. The carbodiimide reagents are normally used in aqueous or organic solvents depending on the particular reagent utilised. The triphenylphosphine/dipyridyldisulphide reagent is suitably used, for example, in organic solvent, usually acetonitrile.

From the foregoing, it may be seen that a compound of formula (II) may be prepared by cyclisation of a compound of formula (XIV) or a compound of formula (III) as hereinabove defined.

Accordingly, the present invention provides a process for the preparation of a compound of the formula (II) or a salt or protected form thereof:

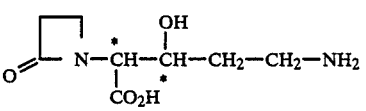  (II)

which process comprises cyclising a compound of the formula (XIVA) or a salt thereof:

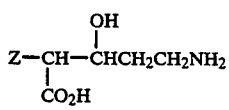

(XIVA)

wherein Z is a group of the formula HO₂CCH₂CH₂NH— or XCH₂CH₂CONH— wherein X is a leaving group; and wherein any reactive groups may be protected; and thereafter if necessary carrying out one or more of the following steps:
(i) removing any protecting groups;
(ii) converting the product into a free acid, salt, or protected form thereof.

A compound of general formula (XIV) may be prepared by reacting 3-hydroxyornithine (V) with a compound of formula (XV):

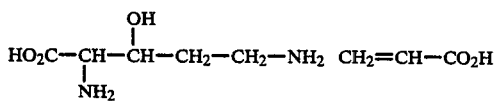

(V)      (XV)

The α-carboxyl and δ-amino groups present in the compound (V) may be protected, for example the 6-amino group may be protected by a benzyloxycarbonyl group.

The carboxyl group of the compound (XV) may be in free form, or in salt form or in another protected form. A suitable protecting group would be, for example, an ester group. In such cases the trichloroethyl ester is normally used. The ester group is usually removed after reaction by using a zinc/acetic acid/tetrahydrofuran mixture.

A compound of formula (II) may also be prepared by conventional β-lactam preparation techniques. For example a compound of formula (XVI):

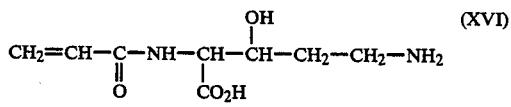

may be converted into a compound of formula (II) in a synthesis using, for example, phenyl sulphenyl chloride followed by potassium hydroxide in conjunction with a phase transfer catalyst. This process is preferably carried out as a 'one-pot' synthesis. In a further method, a compound of formula (XVII) may be reacted with a compound of general formula (V):

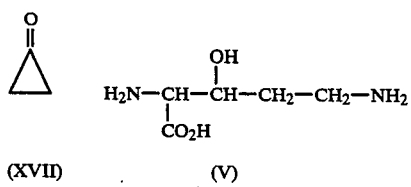

(XVII)     (V)

in a synthesis at a temperature below, for example, −70° C., preferably at −78° C., using first t—C₄H₉OCl, and then silver nitrite, for example. This process is preferably carried out as a one-pot synthesis. In both processes any functional group not involved in the reactions may be protected and, if desired, the protecting group may subsequently be removed.

In the above reaction, where necessary or desired, a free hydroxyl, carboxyl, or amino group of a starting material may be protected by protecting groups customary in the art during the reactions described. The protecting groups may, if desired, be removed by the usual known methods subsequent to the preparation.

The present invention extends to novel intermediates whether in free form or in a form in which one or more functional groups present are in protected form.

From the foregoing it may be seen that the present invention provides a process for the preparation of a compound of the formula (II) or a salt or ester thereof:

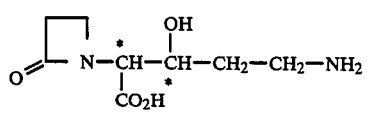

which process comprises treating a compound of the formula (XVIII) or a salt thereof:

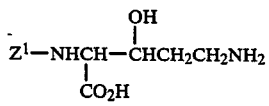

wherein the functional groups may be protected and Z¹ is H or CH₂=CH—CO—; with reagents known in the art to be capable of converting the group Z¹NH— wherein Z¹ is as hereinabove defined into a β-lactam moiety of the formula:

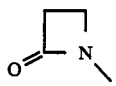

and thereafter if necessary or desired carrying out one or more of the following steps:
(i) removing any protecting groups;
(ii) converting the product into a free acid, salt, or protected form thereof.

Compounds of formulae (IV), (VIII), (IX), (X), (XI), (XI'), (XII), (XV), (XVI) and (XVII) are either known compounds or can be prepared from known compounds by known processes or processes analogous to known processes.

The compound (II) may also be prepared by enzymic synthesis, e.g. a cell free synthesis or by isolation from a suitable strain of a Streptomyces species, for example *S. clavuligerus, S. jumonjinensis, S. katsurahamanus,* or *S. lipmanii.* Suitably, isolation of compound (II) involves disruption of the mycelium and isolation of compound (II) from the cell contents. Typically, isolation of compound (II) in purified form will involve chromatographic procedures. Alternatively, compound (II) may be used in an impure or partially pure form.

It will be understood that a salt of a compound of formula (II) may be prepared by the methods described above wherein a salt of a starting material is used, or a free compound (II) prepared is subsequently converted into a salt. Also, if desired, a salt of compound (II) prepared may be converted into the free unsalified compound or into another salt of compound (II).

The salts of compounds of formula (II) may be produced, for example, by treating a compound of formula (II) with the appropriate acid or base.

Compounds of formula (11) and salts thereof produced by the above processes, may be recovered by conventional methods.

Compounds of general formula (11) may be separated into diastereoisomeric pairs of enantiomers, if so desired, by, for example, fractional crystallisation from a suitable solvent, for example methanol or ethyl acetate or a mixture thereof. The pair of enantiomers thus obtained may be separated into individual stereoisomers by conventional means, for example by the use of an optically active salt as a resolving agent or by stereoselective removal of a protecting group using a suitable enzyme, for example an esterase such as subtilisin. In mixtures of diastereoisomers of formula (II), the ratio of diastereoisomers may be changed by treatment with a non-nucleophilic base, for example 1,5-diazabicyclo[4.3.0]non-5-ene.

Suitable optically active compounds which may be used as resolving agents are described in 'Topics in Stereochemistry', Vol. 6, Wiley Interscience, 1971, Allinger, N. L. and Eliel, W. L., Eds.

Alternatively, any enantiomer of a compound of formula (II) may be obtained by stereospecific synthesis using optically pure starting materials of known configuration.

This invention also extends to a compound of formula (II) or a salt thereof for use in the synthesis of clavulanic acid.

In a further aspect of the pr(R)sent invention, there, is provided a process for the preparation of clavulanic acid or a salt thereof, which process comprises treating a compound of formula (I) or a salt thereof with an enzyme system. There is also provided by the present invention clavulanic acid or a salt thereof whenever prepared by such a process.

Preferably the enzyme system employed is derived from a microorganism, in particular a species of Streptomyces. Suitably the process is carried out in a cell-free system. Suitably the cell-free synthesis of clavulanic acid comprises treating a compound of formula (I) or a salt thereof with an extract of a species of Streptomyces.

Suitably the species of Streptomyces is a clavulanic acid producing species.

The extract from a species of Streptomyces comprises an enzyme system. The cell-free extract is preferably produced by sonication or other disruption of the Streptomyces cells and optionally thereafter removing cell debris leaving the enzyme system in solution or suspension. The enzyme system may be derived from alternative sources; for example the enzyme(s) may suitably be produced by genetic engineering. A preferred enzyme system is derived from a clavulanic acid producing species of Streptomyces such as, for example, clavulanic acid producing strains of S. clavuligerus, S. jumonjinensis and S. katurahamanus or strains derived therefrom, for example mutant strains. In particular the following strains of these microorganisms are suitable: S. clavuligerus ATCC 27064, S. jumonjinensis ATCC 29864 and S. katsurahamanus T-272.

Instead of employing a cell-free system, the above process may also be operated using an intact micro-organism. The precursor compound of formula (I) or a salt thereof is then contacted with the micro-organism to produce clavulanic acid or a salt thereof. The microorganism may be in the form of a growing culture, resting culture, washed mycelium, immobilised cells, or protoplasts.

The enzyme system may be prepared by culturing the microorganism in a conventional manner, especially under aerobic conditions in a suitable liquid or semi-solid medium. In general, carbon and nitrogen sources which microorganisms can assimilate,and inorganic salt nutrients normally used to promote the growth of the microorganisms, are included in the culture medium. The culture conditions may be a temperature in the range of from 10° C. to 80° C. and pH in the range of from 3 to 10. Preferred conditions are from 20° C. to 30° C. at pH of from 5 to 9, for example about pH 7, for 0.5 to 5 days. The enzyme system may be isolated and used in purified form, partially purified form, as obtained in an impure state as a filtrate from a disrupted cell preparation or as a crude cell homogenate.

Most suitably the enzyme system is at least partially purified to remove other enzymes which might catalyse the destruction of the precursor (I), the enzyme(s), or the reaction product. The enzyme(s) may be attached to an insoluble support.

The process is generally carried out in aqueous media, the reaction mixture being maintained in a range of from pH 4 to 9, more suitably for example 6.5 to 8.5. The pH is suitably controlled using conventional buffers known in the art. In one embodiment, for example, 3-(N-morpholino)propanesulphonic acid buffer (pH 7) is used. The temperature of the reaction should be suitable for the enzyme employed and is generally in the range of from 15° C. to 40° C., preferably about 30° C. The reaction time depends on such factors as concentrations of reactants, temperature and pH.

A compound of formula (I) or a salt thereof is for example suitably dissolved in buffer before mixing with the enzyme system; the concentration will depend upon the solubility of the compound of formula (I) or a salt thereof. Suitably the concentration of the solution of compound of formula (I) or a salt thereof may be in the range of 5% w/v to 0.001%/v. After reaction is complete, the enzyme(s) may be separated from the reaction mixture and the clavulanic acid or a salt thereof may be isolated by conventional methods. The initial purification of the clavulanic acid or a salt thereof conveniently involves a chromatography step.

In another embodiment of this invention there is provided a process for converting a precursor of formula (II) or a salt thereof to clavulanic acid or a salt thereof by treatment with an enzyme system as hereinabove described. Suitably the reaction is carried out in a cell-free synthesis without intermediate isolation of the compound (I) or a salt thereof. Alternatively the conversion of the compound of formula (II) into clavulanic acid is carried out directly using an intact micro-organism.

The following Examples illustrate the present invention. All percentages quoted therein are given on a weight basis, and all ratios are given on a volumetric basis. In $^1$H nmr spectra, protons said to be 'exchangeable' exchange for deuterium on shaking with $D_2O$.

EXAMPLE 1

Benzyl 5-azido-3-hydroxy-2-(2-oxoazetidin-1-yl)valerate

Under an atmosphere of dry nitrogen, a solution of benzyl 2-(2-oxoazetidin-1-yl)acetate (3.28 g, 15 mmol) in dry tetrahydrofuran (5 ml) was added to lithium bis(trimethylsilyl)amide (15 ml of a 1M solution in tetrahydrofuran) which had been cooled to −70° C. The rate of addition was such that the temperature of the solution did not rise above −60° C. and, after completion of the addition, the reaction mixture was stirred at −70° C. for 15 minutes. A solution of 3-azidopropionaldehyde (18 mmol) in tetrahydrofuran (5 ml) was added to the reaction mixture whilst maintaining the temperature below −60° C. After stirring at −70° C. for a further 2 hours the reaction mixture was treated with a solution of acetic acid (0.86 ml, 15 mmol) in water (2 ml) and allowed to reach ambient temperature.

The product was extracted into ethyl acetate and washed successively with water, saturated sodium bicarbonate solution and water before being dried (MgSO$_4$) and evaporated to an orange oil. The oil was chromatographed on silica gel (Merck Art. 9385), eluting with ethyl acetate/hexane (2:1), yielding benzyl 5-azido-3-hydroxy-2-(2-oxoazetidin-1-yl)valerate as a pale yellow oil (2.72 g, 36%).

Thin layer chromatography of this material on silica gel plates (Merck Art. 5719) eluting with a mixture of dichloromethane/ethyl acetate/ethanol (60:10:1) indicated a mixture of diastereoisomers in the ratio 1:2, $R_f$ 0.44 and 0.40 respectively; visualisation with iodine vapour. $\nu_{max}$ (KBr) 3107, 2100 and 1733 cm$^{-1}$; $\delta_H$ (CDCl$_3$; 250 MHz) 1.76 (1H,m), 1.96 (1H,m), 3.02 n(2H,m), 3.32 (2H,m), 3.49 (2H,m), 4.03 (1H,d, J 3.3 Hz), 4.28 (1H,m), 4.51 (1H,d, J 5 Hz, exchangeable), 5.23 (2H,s) and 7.34 (5H,s).

EXAMPLE 2

Epimerisation of benzyl 5-azido-3-hydroxy-2-(2-oxo-azetidin-1-yl)valerate

To a solution of benzyl 5-azido-3-hydroxy-2-(2-oxoazetidin1-yl)valerate (4.11g, 12.8 mmol) prepared as in Example 1, in dichloromethane (400 ml), 1,5-diazabicyclo[4.3.0]non-5-ene (1.86 g, 14.9 mmol) was added and the mixture stirred at room temperature for one hour. The solvent was removed under reduced pressure and half of the residual oil chromatographed on a column (45×4.5 cm) of silica gel (Merck Art. 9385) using a mixture of dichloromethane, ethyl acetate and ethanol (60:10:1) to yield the faster moving diastereoisomer of benzyl 5-azido-3-hydroxy-2-(2-oxoazetindin-1-yl)valerate (1.1 g) as an oil, which crystallised on standing, and a mixture of the faster and slower moving diastereoisomers in the ratio 30:70 respectively (58 mg) as an oil. Chromatography of the other half of the reaction mixture under the same conditions produced further similar quantities of the fast moving diastereoisomer and the mixture of the two diastereoisomers. A sample of faster moving diastereoisomer was recrystallised from hexane to yield white needles m.p. 63°-64°. $\nu_{max}$ (KBr) 3400, 2101, 1725, 1263, 752, 699 cm$^{-1}$. $\delta_H$(CDCl$_3$, 400 MHz), 1.7 (1H, m), 1.84 (1H, m), 3.03 (2H, m), 3.35 (1H, m), 3.43 (1H, m), 3.51 (2H, m), 4.04 (1H, d, J 3 Hz), 4.32 (2H, m), 5.23 and 5.26 (2H, ABq, J 12 Hz), and 7.37 (5H, s). (Found: C, 56.63; 5.64; N, 17.50%. C$_{15}$H$_{18}$N$_4$O$_4$ requires C, 56.59; H, 5.70; N, 17.60%).

The slow moving diastereoisomer of benzyl 5-azido-3-hydroxy-2-(2-oxoazetidin-1-yl)valerate was obtained as an oil by chromatography, using the same system, of samples containing a proportion of that diastereoisomer. $\delta_H$(CHCl$_3$, 250 MHz), 1.78 (1H, m), 1.97 (1H, m), 2.99 (2H, t, J 4.5 Hz), 3.33 (2H, m), 3.5 (2H, m), 4.04 (1H, d, J 4.5 Hz), 4.27 (1H, m), 4.52 (1H, d, J 5 Hz), 5.22 (2H, m) and 7.36 (5H, s).

The slow moving diastereoisomer may be isomerised to a mixture of the faster moving diastereoisomer and slower moving diastereoisomer in the ratio 3:1 respectively by treatment with 1,5-diazabicyclo[4.3.0]non-5-ene as described above.

The two diastereoisomers are readily assayed using a hplc system consisting of a Spherisorb silica column, eluting with a mixture of acetonitrile, acetic acid and dichloromethane in the proportions 8:0.1:91.9 and UV detection at 254 nm.

EXAMPLE 3

Resolution of the fast moving diastereoisomer of benzyl 5-azido-3-hydroxy-2-(2-oxoazetidin-1-yl)valerate The fast moving diastereoisomer of benzyl 5-azido-3-hydroxy-2-(2-oxoazetidin-1-yl)valerate (300 mg, 0.94 mmol) was dissolved in acetone (5.5 ml) and 0.1 M phosphate buffer (25 ml) and stirred at 37° C. Subtilisin Carlsberg (50 mg, obtained from Sigma Chemical Co. Ltd.) was added and the reaction mixture maintained at pH 7.6 with 1M sodium hydroxide solution using a Metrohm pH Stat. When no more sodium hydroxide solution was being used, after about five and a half hours, the pH of the solution was adjusted to pH 9.5 and the solution extracted with ethyl acetate. The organic layer was washed with water and dried (MgSO$_4$) to yield unhydrolysed ester (142 mg). The aqueous fraction was acidified to pH 3.0 using dilute hydrochloric acid and extracted with ethyl acetate to yield, after drying (MgSO$_4$) an unstable oil, 5-azido-3-hydroxy-2-(2-oxoazetidin-1-yl)valeric acid (83 mg).

A sample of unhydrolysed ester was purified by column chromatography on silica gel (Merck Art. 9385) using ethyl acetate/hexane/ethanol (40:60:2) eluant to yield enantiomerically pure benzyl 5-azido-3-hydroxy-2-(2-oxoazetidin-1-yl)valerate. $[\alpha]_D^{20}$+31.8° (C 2.0; CHCl$_3$); $^1$H nmr spectrum identical to starting material.

EXAMPLE 4

Ethyl 5-azido-3-hydroxy-2-(2-oxoazetidin-1-yl)valerate

A solution of ethyl 5-chloro-3-hydroxy-2-(2-oxoazetidin-1-yl)valerate (3.45 g, 13.8 mmol) and sodium azide (1.10 g, 17 mmol) in dry dimethylsulphoxide (20 ml) was stirred between 55° and 65° C. for 5 hours. The reaction mixture was diluted with dichloromethane and the organic layer was washed three times with water before being dried (MgSO$_4$) and evaporated. The residue was chromatographed on silica gel (Merck Art. 9385), eluting with ethyl acetate/hexane (2:1), to give ethyl 5-azido-3-hydroxy-2-(2-oxoazetidin-1-yl)valerate as a pale yellow oil in 73% yield (2.59 g). Bulb to bulb distillation at 0.2 mmHg between 185°-195° C. further purified the product to a colourless oil. $\nu_{max}$ (KBr) 3405, 2102 and 1733 cm$^{-1}$; $\delta_H$ (CHCl$_3$, 250 MHz) 1.31 (3H,t,J 7 Hz), 1.81 (1H,m), 1.87 (1H,m), 3.03 (2H,t,J 3 Hz), 3.40 (2H,m), 3.53 (2H,m), 4.00 (1H,d,J 3.5 Hz), 4.25 (3H,m) and 4.53 (1H,d,J 4.5 Hz, exchangeable). (Found: C, 46.93; H, 6.46; N, 21.83%. C$_{10}$H$_{16}$N$_3$O$_4$ requires C, 46.87; H, 6.29; N, 21.86%).

EXAMPLE 5

5-Azido-3-hydroxy-2-(2-oxoazetidin-1-yl)valeric acid

A solution of ethyl 5-azido-3-hydroxy-2-(2-oxoazetidin-1-yl)valerate (0.77 g, 3 mmol) in tetrahydrofuran (13 ml) and water (13 ml) was treated with a solution of potassium carbonate (0.445 g, 3.2 mmol) in water (2.5 ml) in such a way that the pH of the reaction mixture did not rise above 11.5. After evaporation of the solvent the product was extracted into ethanol, filtered and chromatographed on silica gel (Merck Art. 9385) eluting with ethanol to give a white solid (396 mg). This material (200 mg) was dissolved in water and passed through a column of IR 120(H) ion exchange resin to give 5-azido-3-hydroxy-2-(2-oxoazetidin-1-yl)valeric acid (92 mg) as an oil which slowly gave a white solid. The compound was used without further purification. $\delta_H$ [(CD$_3$)$_2$SO+D$_2$O] 1.69 (2H,m), 2.89 (2H,t,J 3 Hz) 3.40 (4H,m), 3.89 (1H,m) and 4.10 (1H,d, J 6.6 Hz).

EXAMPLE 6

Ethyl 5-chloro-3-hydroxy-2-(2-oxoazetidin-1-yl)valerate

Under an atmosphere of dry nitrogen, a solution of ethyl 2-(2-oxoazetidin-1-yl)acetate (8.45 g, 54 mmol) in dry tetrahydrofuran (20 ml) was added to lithium bis(trimethylsilyl)amide (55 ml of a 1 M solution in tetrahydrofuran) which had been cooled to −70° C. The rate of addition was such that the temperature of the solution did not rise above −60° C. and after completion the reaction mixture was stirred at −70° C. for 15 minutes. A solution of 3-chloropropionaldehyde (65 mmol) in ether (90 ml) was added to the reaction mixture whilst maintaining the temperature below −60° C. After stirring at −70° C. for a further 2 hours the reaction mixture was treated with a solution of acetic acid (3.5 ml) in water (3 ml) and allowed to reach ambient temperature.

The product was extracted into ethyl acetate and washed successively with water, saturated sodium bicarbonate solution and water before being dried (MgSO$_4$) and evaporated to an oil. The oil was chromatographed on silica gel (Merck Art. 9385) eluting with ethyl acetate/hexane (2:1) and yielded ethyl 5-chloro-3-hydroxy-2-(2-oxoazetidin-1-yl)valerate as an oil in 29% yield (3.90 g) with a 5% recovery of ethyl 2-(2-oxoazetidin-1-yl) acetate.

The product could be further purified by bulb to bulb distillation at 0.3 mmHg between 170°–180° C. $\nu_{max}$ (KBr) 3383 and 1734 cm$^{-1}$; $\delta_H$ (CDCl$_3$, 60 MHz) 1.31 (3H,t,J 6 Hz), 2.09 (2H,m), 3.03 (2H,m), 3.39 (2H,m), 3.70 (2H,m) and 4.25 (5H,m, one proton exchangeable). (Found: C, 48.5; H, 6.8; N, 5.7%. C$_{10}$H$_{16}$ClNO$_4$ requires C, 48.1; H, 6.5; N, 5.6%).

EXAMPLE 7

Benzyl N5-benzyloxycarbonyl-3-hydroxyornithinate hydrochloride

To a stirred solution of benzyl N-(diphenylmethylene) glycinate (3.6 g; 11 mmol) in 15 ml dry tetrahydrofuran under dry nitrogen cooled to −70° C., a solution of lithium bis(trimethylsilyl)amide (11 ml of a 1 M solution in THF) was added dropwise over 20 minutes so that the temperature of the reaction mixture did not rise above −60° C. The reaction mixture was stirred at −70° C. for 20 minutes then a solution of N-benzyloxycarbonyl-3-aminopropionaldehyde (3 g; 14.5 mmol) in 15 ml dry tetrahydrofuran added dropwise, again, keeping the temperature below −60° C. The reaction was then stirred for a further 7 minutes at −70° C. The reaction mixture was allowed to warm to −20° C. then poured into a well stirred mixture of ether (100 ml) and phosphate buffer at pH 7.0 (100 ml). The ether layer was separated and the aqueous phase extracted with ether (2×50 ml). The combined organic extracts were washed with water, dried (MgSO$_4$) and evaporated to yield an oil (7.2 g). The $^1$H nmr spectrum of this material indicated it to be substantially pure benzyl N$^2$-diphenylmethylene-N$^5$-benzyloxycarbonyl- 3-hydroxy- ornithinate. The compound was dissolved in ether (25 ml), 2N HCl added (25 ml) and the reaction mixture stirred vigorously at room temperature for 2 hours. The reaction mixture was filtered to yield a mixture of diastereoisomers of benzyl N$^5$-benzyloxycarbonyl-3- hydroxyornithinate hydrochloride as a pale yellow solid (2.4 g). Recrystalliation of a sample (300 mg) of this material from EtOH yielded the less-soluble diastereoisomer (110 mg) m.p. 195°–197°, $\nu$max (KBr) 3300 1708 1691 1272cm$^{-1}$; $\delta_H$[(CD$_3$)$_2$ SO] 1.69 (2H, m); 3.1 (2H, m), 3.98 (1H, m), 4.11 (1H, d, J 2.5 Hz), 5.0 (2H, s), 5.18 (1H, d, J 12.5 Hz), 5.28 (1H, d, J 12.5 Hz), 5.77 (1H, d, J 5 Hz), 7.36 (10H, m), 8.53 (3H, br. s). (Found: C, 58.67, H, 5.96; N, 6.67; Cl, 8.76%. C$_{20}$H$_{25}$ClN$_2$O$_5$ requires C, 58.74; H, 6.16; N, 6.85; Cl, 8.76%).

Evaporation of the ethanol from the filtrate and trituration of the residue with ethyl acetate gave a further quantity of the less-soluble diastereoisomer (100 mg), after filtration. Evaporation of the filtrate yielded the more-soluble diastereoisomer of benzyl N$^5$-benzyloxycarbonyl-3-hydroxyornithinate hydrochloride as a gum; $\delta_H$[(CD$_3$)$_2$SO] 1.67 (H, m), 3.14 (2H, m), 4.10 (2H, m), 4.99 (2H, s), 5.20 (1H, d, J 12.5 Hz), 5.30 (1H, d, J 12.5 Hz), 5.80 (1H, d, J 5 Hz), 7.38 (10H, m) and 8.44 (3H, br. s) contaminated with a small amount of the less-soluble diastereoisomer.

A further quantity of the mixed diastereoisomers was recovered from the acid solution remaining after the hydrolysis of benzyl N$^2$-diphenylmethylene-N$^5$-benzyloxycarbonyl-3-hydroxyornithinate. The acid solution was separated from the ether phase, the pH adjusted to 6.0, and the water removed by evaporation. Ethanol was added to the gummy residue and evaporated to yield a gum (1.5 g). Trituration of the gum with acetone, filtration of the solids and evaporation of the acetone filtrate yielded a mixture of diastereoisomers of benzyl N$^5$-benzyloxycarbonyl-3-hydroxyornithinate hydrochloride (500 mg), the more-soluble diastereoisomer predominating. Separation of the diastereoisomers was achieved by trituration with ethyl acetate. Total yield of benzyl N$^5$-benzyloxycarbonyl-3-hydroxyornithinate hydrochloride 2.9 g (65%).

EXAMPLE 8

Benzyl N$^2$-($\beta$-carboxyethyl)-N$^5$-benzyloxycarbonyl-3-hydroxyornithinate A solution of benzyl N$^5$-benzyloxycarbonyl-3-hydroxyornithinate hydrochloride containing approx. 90% less-soluble diastereoisomer and approx. 10 % more-soluble diastereoisomer (1.0 g, 2.4 mmol) in water (15 ml) was stirred with ethyl acetate (150 ml) and adjusted to pH 7.75 with a dilute solution of sodium hydroxide. The aqueous layer was separated and extracted with ethyl acetate (3×100 ml). The combined organic layers were dried (MgSO$_4$) and evaporated to yield benzyl N$^5$-benzyl-oxycarbonyl-3-hydroxyornithinate (0.57 g) as a partially crystalline oil. A sample of this material (430 mg, 1.15 mmol) was dissolved in distilled acetonitrile (15 ml) containing acrylic acid (0.788 ml, 11.5 mmol) and stirred at room temperature for three days. The resulting white precipitate was filtered off and washed with a few millilitres of acetonitrile to provide benzyl $N^2$-($\beta$-carboxyethyl)-$N^5$-benzyloxycarbonyl-3-hydroxyornithinate (390 mg 76 %), m.p. 153.5–154.5 (acetonitrile), $\nu_{max}$ (KBr) 3336, 1740, 1691, 1633, 1533, 750 and 698 cm$^{-1}$; $\delta_H$[(CD$_3$)$_2$SO; 250 MHz] 1.45 (1 H, m), 1.73 (1H, m), 2.31 (2H, t, J 6.6 Hz), 2.56 (1H, m), 2.74 (1H, m), 3.06 (3H, m), 3.37 (2H, br s), 3.63 (1H, m), 5.00 (2H, s), 5.12 (2H, s), 7.19 (1H, t, J 5.3 Hz) and 7.35 (lOH, m). (Found: C, 61.86; H, 6.18; N, 6.21%; MH+, (p.i. F.A.B., thioglycerol), 445. $C_{23}H_{28}N_2O_7$ requires C, 62.15; H, 6.35; N, 6.30%; M, 444).

EXAMPLE 9

Benzyl 5-benzyloxycarbonylamino-3-hydroxy-2-(2-oxoazetidin-1-yl)valerate

Benzyl $N^2$-($\beta$-carboxyethyl)-$N^5$-benzyloxycarbonyl-3-hydroxyornithinate (227 mg, 0.51 mmol) in distilled acetonitrile (50 ml) was heated under reflux with recrystallised 2,2'-dipyridyl disulphide (135 mg, 0.61 mmol) and triphenylphosphine (160 mg, 0.61 mmol) for eight hours. The acetonitrile was removed under vacuum and the residue chromatographed over silica gel (Merck Art. 9385) repeatedly using the following solvents as eluants ether/ethanol (49:1), ethyl acetate/isopropyl alcohol (19:1) and hexane/acetone/isopropyl alcohol (8:8:1) to yield the slow-moving diastereoisomer of the title compound as an oil (217 mg, 64%) which slowly crystallised m.p. 66°–68° (ethyl acetate/hexane); [Rf 0.22 on thin layer chromatography, silica gel plates (Merck Art. 5719) eluting with dichloromethane/ethyl acetate/ethanol (60:10:1)]. $\nu_{max}$(KBr) 1725, 742, and 698 cm$^{-1}$; $\delta_H$(CDCl$_3$, 250 MHz) 1.85 (2H, m), 2.98 (2H, t, J 4.2 Hz), 3.40 (4H, m), 4.09 (1H, d, J 3.3H), 4.17 (1H, m), 4.69 (1H, d, J4.1Hz) (exchanges with D$_2$O), 5.10 (2H, s) 5.22 (3H, m) and 7.36 (10 H, m). [Found: C, 64.81; H, 6.12; N, 6.55 %; MH+ (p.i. F.A.B. thioglycerol) 427. $C_{23}H_{26}N_2O_7$ requires C, 64.77; H, 6.15; N, 6.57%; M, 426].

EXAMPLE 10

Epimerisation of benzyl 5-benzyloxycarbonylamino-3-hydroxy-2-(2-oxoazetidin-1-yl)valerate The slow moving diastereoisomer of the title compound (0.7 mg, 1.6 $\mu$mol), prepared as described in Example 9, was treated with 1,5-diazabicyclo[4.3.0]non-5-ene (0.25 $\mu$l, 2.0 $\mu$mol) in dichloromethane (350 $\mu$l) as in Example 2. Analysis of the reaction mixture after ninety minutes by high pressure liquid chromatography (column: Spherisorb 5 $\mu$M silica, eluting with ethyl acetate-hexane-acetic acid (50:49.85:0.15) mixture; flow, 1.5 ml/min; detection, UV at 254 nm) showed conversion to a mixture of the faster moving diastereoisomer (retention time 9.7 min) and the slower moving diastereoisomer (retention time 11.1 min) in the ratio 71:29 respectively. The faster moving diastereoisomer may be separated from a mixture of both diastereoisomers by chromatography on silica gel (Merck Art. 9385) eluting with dichloromethane/ethyl acetate/ethanol (60:10:1). On thin layer chromatography, silica plates (Merck Art. 5719), the faster diastereoisomer had an Rf 0.25; the slow diastereoisomer had an Rf 0.22 in the same solvent system. The faster diastereoisomer shows the following spectral properties; $\nu_{max}$ (KBr) 1725, 1527, 752 and 698; 67 $_H$ (CDCl$_3$, 250 MHz) 1.70 (2H, m), 3.01 (2H, t, J 4 Hz), 3.37 (4H, m), 4.34 (1H, d, J 3 Hz), 4.28 (1H, m) 4.49 (1H, d, 8.4 Hz), 5.10 (3H, m), 5.21 (2H, m) and 7.35 (10H, m).

EXAMPLE 11

Benzyl 5-benzyloxycarbonylamino-3-oxo-2-(2-oxoazetidin-1-yl)valerate

Benzyl 2-(2-oxoazetidin-1-yl)acetate (1.25 g 5.7 mmol) was dissolved in dry tetrahydrofuran (40 ml) and cooled to $-60°$ C. under dry nitrogen. Lithium bis(trimethyl-silyl)amide (6.27 ml of 1.0M solution in hexane) was added dropwise over ten minutes and the mixture stirred at $-60°$ C. for a further fifteen minutes. $\beta$-Benzyloxycarbonylaminopropionyl chloride (2.41 g, 1O mmol) in dry tetrahydrofuran (10 ml) was added over 15 minutes and the mixture stirred at $-60°$ C. for a further two and a half hours.

Acetic acid (0.5 ml) and ethyl acetate (400 ml) was added to the reaction mixture which was then washed with water (50 ml), brine (50 ml), saturated sodium bicarbonate solution (50 ml) and dried (MgSO$_4$). The solvent was evaporated at low temperature under vacuum and the crude product purified by column chromatography using silica gel (Merck Art. 9385) eluting with ethyl acetate to yield benzyl 5-benzyloxycarbonylamino-3-oxo-2-(2-oxoazetidin-1-yl)valerate (0.415 g 17.1%) as a gum. $\nu_{max}$ (KBr) 3382, 1760, 1719, 1522 and 1247; $\delta$(CDCl3, 250 MHz) 2.58 (1H, t, 7 Hz), 2.9 (2H, m), 3.1 (1H, m), 3.4 (3H, m), 4.0 (1H, m), 5.07 (2H, s), 5.20 (2H, s) and 7.35 (10H, m).

EXAMPLE 12

Benzyl 5-benzyloxycarbonylamino-3-hydroxy-2-(2-oxo-azetidin-1-yl)valerate

Benzyl 5-benzyloxycarbonylamino-3-oxo-2-(2-oxoazetidin-1-yl)valerate (6.9 mg, 16 $\mu$mol) in tetrahydrofuran (1.5 ml) was treated with sodium borohydride (2.2 mg, 58 $\mu$mol). After one hour the reaction mixture was analysed by high pressure liquid chromatography using similar conditions to those described in Example 10. The reaction mixture contained the fast moving diastereoisomer of the title compound and slow moving diastereoisomer of the title compound in the ratio 55:45 respectively together with unreacted starting material.

EXAMPLE 13

Preparation of 5-amino-3-hydroxy-2-(2-oxo-azetidin-1-yl)valeric acid

Benzyl 5-azido-3-hydroxy-2-(2-oxo-azetidin-1-yl)-valerate (1.6 g, 5 mmol) as a mixture of diastereoisomers prepared as Example 1, was hydrogenated at atmospheric pressure in ethanol (45 ml) and water (7 ml) with 5% palladium on carbon catalyst (900 mg). When no more hydrogen was absorbed the reaction mixture was filtered and the filtrate evaporated to yield a gum. Trituration with ether yielded a solid which was filtered off and dried under vacuum to yield a friable foam. The foam was triturated with methanol to give a white solid and pale yellow solution. The solid was filtered off and dried to yield the less soluble diastereoisomer of the title compound (294 mg) as a white powder m.p. 152°–153.5°. $\nu_{max}$ (KBr) 3422, 1709, 1637, 1578, 1376, 1333, 1248, 1228 and 1151; $\delta_H$ (D$_2$O, 250 MHz) 1.93 (2H, m), 3.03 (2H, t, J 4 Hz), 3.21 (2H, m), 3.55 (2H, m), and 4.21 (2H, m); $\delta_C$ (D$_2$O, 100 MHz) 31.06, 36.23, 37.99, 41.03, 62.49, 69.54, 172.40 and 174.74. (Found: C, 45.85, H, 6.77; N, 12.94 %; $C_8H_{14}N_2O_4\frac{1}{2}H_2O$ requires C, 45.49; H, 7.16; N, 13.26 %).

The pale yellow methanol solution was evaporated to yield a mixture of the less soluble diastereoisomer described above and the more soluble diastereoisomer as a powder (574.2 mg). 2D Carbon-proton nuclear magnetic resonance correlation experiment ($\delta_C : \delta_H$); 30.9, 1.90; 31.5, 1.84; 36.2, 2.95; 37.8, 3.15; 41.0, 3.44; 41.0, 3.56; 62.39, 4.18; 62.89, 4.13; 69.47, 4.16 and 69.47, 4.26.

EXAMPLE 14

Preparation of
5-amino-3-hydroxy-2-(2-oxoazetidin-1-yl)valeric acid

The fast moving diastereoisomer of benzyl 5-azido-3-hydroxy-2-(2-oxoazetidin-1-yl)valerate (0.76 g, 23.9 mmol) was hydrogenated over 5% palladium on carbon catalyst in ethanol (20 ml) and water (5 ml) for one hour. The catalyst was filtered off and the filtrate evaporated. The residual gum was triturated with ether to yield, after filtration the title compound as a pale yellow solid (456 mg, 97%). The yellow coloured impurity was removed by trituration with ethyl acetate. The title compound (400 mg) was further purified by column chromatography on silica gel (Merck Art. 9385) using water/ethanol (15:85) as eluant to yield the title compound (290 mg) as a white solid containing 1/7 molar equivalent of ethanol. $\delta H$ ($D_2O$, 400 MHz) 1.16 (t, $CH_3CH_2OH$), 1.84 (2H, m), 3.00 (2H, t, J 3.9 Hz), 3.15 (2H, m), 3.50 (1H, m), 3.58 (1H, m), 3.63 (q, $CH_3CH_2OH$), 4.07 (1H, d, J 5.4 Hz), 4.19 (1H, m), $\delta_C$ ($D_2O$, 100 HMz), 31.66, 36.12, 37.61, 40.99, 63.19, 69.54, 174.79, and 174.97. Recrystallisation of a sample from aqueous methanol gave white prisms m.p. 130°–135°. $\nu_{max}$ (KBr) 3349, 1723, 1653, 1611, 1390, 918 and 769. (Found: C, 43.93; H, 7.40; N, 12.49%. $C_8H_{14}N_2O_4.H_2O$ requires C, 43.63; H, 7.32; N, 12.72)

EXAMPLE 15

5-Amino.3-hydroxy-2-(2-oxoazetidin-1-yl)valeric acid from enantiomerially pure benzyl
5-azido-3-hydroxy-2-(2-oxo-azetidin-1-yl)valerate Enantiomerically pure benzyl 5-azido-3-hydroxy-2-(2-oxo-azetidin-1-yl)valerate (140 mg), $[\alpha]_D^{20}+31.8°$ (C 2.0, CHCl$_3$) obtained by treatment of the fast moving diastereoisomer with subtilisin Carlsberg as described in Example 3, was hydrogenated in ethanol (7 ml) and water (2 ml) over 5% palladium on carbon catalyst (75 mg). After filtration the solution was evaporated to yield an oil which dissolved in methanol, filtered and the filtrate evaporated to yield 5-amino-3-hydroxy-2-(2-oxoazetidin-1-yl)valeric acid as a white solid (61 mg) $[\alpha]_D^{20}+7.00$ (C 0.5 %; H$_2$O). $^1$H nmr corresponded to the compound prepared in Example 14.

EXAMPLE 16

Benzyl 2-(2-oxo-[2-$^{13}$C]azetidin-1-yl)-[1,2-$^{13}$C$_2$]acetate (a) Tosylate salt of benzyl [1,2-$^{13}$C$_2$]glycinate

[1,2-$^{13}$C$_2$]-Glycine (1.1 g, 14.3 mmol), 99.5 atom % $^{13}$C at each position, in benzyl alcohol (7 ml, 67.6 mmol) and toluene (20 ml) was heated under reflux with p-toluene sulphonic acid (3. g, 16.3 mmol) using a Dean and Stark apparatus for three and a half hours. The reaction mixture was cooled and poured into stirred ether (150 ml). The resulting crystalline solid was filtered off, washed with ether (15 ml) and dried to yield (4.51 g, 93 %) of the tosylate salt of benzyl [1,2-$^{13}$C$_2$]glycinate.

m.p. 130°–132° (lit. unlabelled compound 132°–134°). $\nu_{max}$ (KBr) 1707, 1223, 1181 and 687 cm$^{-1}$, $\delta_H$ [(CD$_3$)$_2$SO, 250 MHz] 2.30 (3H, s), 3.90 (2H, dd, J 144.8 and 6.5 Hz), 5.25 (2H, d, J 3.5 Hz), 7.30 (4H, dd, J 92 and 8.0 Hz), 7.40 (5H, m) and 8.25 (3H, br s). $\delta_C$ [(CD$_3$)$_2$SO, 100 MHz], 39.7 (d, J 62.1 1 Hz), 167.5 (d, J 62.1 Hz).

The material was judged to be 99.5 atom % $^{13}$C at positions 1 and 2 in the glycine moiety from the $^{13}$C nmr spectrum.

(b) Benzyl N-(3-bromo-[1-$^{13}$C]propionyl)-[1,2-$^{13}$C$_2$]-glycinate

The tosylate salt of benzyl [1,2-$^{13}$C$_2$]glycinate (3.23 g, 9.52 mmol) prepared as above, in a mixture of water (15 ml) and tetrahydrofuran (15 ml) was stirred vigorously at 4° C. whilst a solution of 3-bromo-[1-$^{13}$C]-propionyl chloride (1.64 g, 9.51 mmol, 91 atom % $^{13}$C), prepared by standard methods, in tetrahydrofuran (5 ml) was added dropwise over ten minutes. The pH of the reaction mixture was maintained in the range 5.5–6.5 with dilute sodium hydroxide solution during the addition and for a further forty-five minutes. The reaction mixture was diluted with ethyl acetate (150 ml), the organic phase separated and washed with saturated brine and dried (MgSO$_4$). Evaporation of the dried solution gvve a white solid which after trituration with hexane (30 ml) gave benzyl N-(3-bromo-[1-$^{13}$C]propionyl)-[1,2-$^{13}$C$_2$]-glycinate (2.7 g, 94 %). m.p. 62.5°–64.0°; $\nu_{max}$ (KBr) 3309, 1694, 1611, 1537, 755 and 701cm$^{-1}$; $\delta_H$[(CDCl$_3$), 250 MHz]2.83 (2H, m), 3.63 (2H, m), 4.13 (2H, dddd, J 141.5, 7.9, 5.4 and 2.8 Hz), 5.20 (2H, d, J 3.2 Hz), 6.10 (1H, br s) and 7.36 (5H, s); $\delta_C$ (CDCl$_3$, 100 MHz) 41.5 (d, J 61.6 Hz), 169.6 (dd, J 61.8 and 2 Hz) and 169.7 (d, J 2 Hz). (Found: C, 48.26; H, 4.65; N, 4.62%; M$^+$, 302.0254. $C_9{}^{13}C_3H_{14}NO_3Br$ requires C, 48.53, H, 4.65; N, 4.62%, M, 302.0259).

(c) Benzyl
2-(2-oxo-[2-$^{13}$C]azetidin-1-yl)-[1,2-$^{13}$C$_2$]acetate

Powdered potassium hydroxide (1.05 g, 18.7 mmol) and tetrabutylammonium bromide (0.78 g, 2.4 mmol) were dried at 100° in a vacuum for two hours cooled and suspended in a mixture of dichloromethane and acetonitrile (19:1; 300 ml). The mixture was stirred vigorously and sonicated at 30°–40° and benzyl N-(3-bromo-[1-$^{13}$C]-propionyl)-[1,2-$^{13}$C$_2$]glycinate (2.5 g, 8.2 mmol) in dichloromethane/acetonitrile (19:1; 300 ml) added over five hours. The reaction mixture was stirred and sonicated for a further fifteen minutes, the insoluble material filtered off and the filtrate evaporated to dryness. The resulting oil was extracted thoroughly with ether (2×80 ml) and the combined ethereal layers evaporated. Chromatography of the residue on silica gel (Merck Art. 9385) with ethyl acetate/hexane (1:1) yielded the starting material benzyl N-(3-bromo-[1-$^{13}$C]- propionyl)-[1,2-$^{13}$C$_2$]glycinate (0.84 g, 33%) and benzyl 2-(2-oxo-[2-$^{13}$C]azetidin-1-yl)-[1,2-$^{13}$C$_2$]acetate as an oil (0.36 g, 20%). $\nu_{max}$ (KBr) 1700, 742 and 700cm$^{-1}$; $\delta_H$ (CDCl$_3$, 250 MHz) 3.04 (2H, dt, J 6 and 4.1 Hz), 3.43 (2H, m), 3.75 (1H, m), 4.31 (1H, m), 5.18 (2H, d, J 3.1 Hz) and 7.37 (5H, m); $\delta_C$ (CDCl$_3$, 100 MHz) 43.12 (dd, J 62.1 and 0.9 Hz), 167.84 (m) and 168.1 (dd, J 62.3 and 1.2 Hz) (Found: M+222.0996, $C_9{}^{13}C_3H_{13}NO_3$ requires M, 222.0996).

EXAMPLE 17

Benzyl 5-azido-3-hydroxy-2-(2-oxo-[2-$^{13}$C]azetidin-1-yl)-[1,2-$^{13}$C$_2$]valerate The title compound was prepared by reacting benzyl 2-(2-oxo-[2-$^{13}$C]azetidin-1-yl)-[1,2-$^{13}$C$_2$]acetate with 3-azidopropionaldehyde as described in Example 1, epimerising the resultant product with 1,5-diazabicyclo[4.3.0]non-5-ene as described in Example 2 and separating the fast moving diastereoisomer by chromatography. The mixture of fast and slow moving diastereoisomers recovered from the chromatographic column was further isomerised to yield an additional quantity of the pure fast moving diastereoisomer of the title compound. The overall yield of the fast moving diastereoisomer of the title compound was 36%. $\nu_{max}$ (KBr) 2102, 1696, 1668, 761 and 704 cm$^{-1}$; $\delta_H$ (CDCl$_3$, 400 MHz), 1.71 (1H, m), 1.83 (1H, m), 3.03 (2H, m), 3.34 (1H, m), 3.43 (1H, m), 3.51 (2H, m), 3.87 (½H, m), 4.22 (½H, m), 4.26 (1H, m), 4.34 (1H, m), 5.23 (2H, m) and 7.36 (5H, m); $\delta_C$ (CDCl$_3$, 100 mHz) 63.4 (d, J 61.3 Hz), 168.1 (d, J 61.2 Hz) and 169.3. (Found: M+322.1506. C$_{12}$$^{13}$C$_3$H$_{18}$N$_4$O$_4$ requires M, 322.1508).

EXAMPLE 18

5-Amino-3-hydroxy-2-(2-oxo-[2-$^{13}$C]azetidin-1-yl)-[1,2-$^{13}$C$_2$]valeric acid The fast moving diastereoisomer of benzyl 5-azido-3-hydroxy-2-(2-oxo[2-13C]azetidin-1-yl)-[1,2-13C2]-valerate was reduced with hydrogen in the presence of 5% palladium on carbon as Example 14 to yield the title compound as a hygroscopic powder. $\nu_{max}$ (KBr) 3424, 1678, 1544 and 1355 cm$^{-1}$; $\delta_H$ (D$_2$O, 250 Mz) 1.85 (2H, m), 3.0 (2H, m), 3.15 (2H, m), 3.55 (2H, m), 3.80 (½H, m), 4.19 (1H, m) and 4.34 (½H, m); $\delta_C$(D$_2$O, 100 MHz) 63.20 (d, J 54 Hz), 172.6 and 174.97 (d, J 53 Hz). (Found: MH+(p.i. F.A.B. thioglycerol) 206. C$_5$$^{13}$C$_3$H$_{14}$N$_2$O$_4$ requires M 205]. The degree of $^{13}$C enrichment as judged from the 13C nmr spectrum was 99.5% at positions 1 and 2 of the valeric acid moiety and to a comparable degree at the 2 position of the azetidin-1-yl moiety.

EXAMPLE 19

Preparation of media for the cultivation of *Streptomyces clavuligerus* and *Streptomyces lipmanii*

The organisms used for the experiments described in the examples were a reisolate of *Streptomyces clavuligerus* ATCC 27064, *Streptomyces lipmanii* NRRL 3584, *Streptomyces jumonjinensis* ATCC 29864 and *Streptomyces katsurahamanus* T-272. The cultures may be grown on solid or liquid media.

Solid Media
The agar described below is suitable.

| | |
|---|---|
| Hydrolysed Starch (Dextrin, Corn Products, Trafford Park, Manchester) | 10 g |
| KH$_2$PO$_4$ | 1 g |
| MgSO$_4$.7H$_2$O | 1 g |
| NaCl | 1 g |
| CaCO$_3$ | 4 g |
| (NH$_4$)$_2$SO$_4$ | 1 g |
| Trace element solution+ | 1 ml |
| Agar (Oxoid No. 3) | 20 g |
| Make up to 1 L with deionised water. | |

Liquid Media
Suitable liquid culture media are:-

| | |
|---|---|
| Seed Medium A | |
| Soya bean flour (Arkasoy 50, British Arkady Co., Arkady Soya Mills, Old Trafford, Manchester) | 20 g |
| Hydrolysed Starch (Dextrin Corn Products) | 10 g |
| KH$_2$PO$_4$ | 0.6 g |
| Glyceryl trioleate (Estol 1434, Price's Chemicals Ltd, Bebington, Wirral Merseyside) | 5.0 g |
| Make up to 1 L with tap water and adjust to pH 7.0 with NaOH solution. | |
| Seed Medium B | |
| Malt extract (Oxoid Ltd, Basingstoke, Hants) | 10 g |
| Bacteriological peptone (Oxoid Ltd) | 10 g |
| Glycerol | 20 g |
| Make up to 1 L with tap water and adjust to pH 7.0. | |
| Production Medium A | |
| Soya Bean Flour (Arkasoy 50, British Arkady Co.) | 35 g |
| Hydrolysed Starch (Dextrin, Corn Products) | 50 g |
| KH$_2$PO$_4$ | 0.7 g |
| Glycerol | 5.0 g |
| Trace element solution* | 10 ml |
| Make up to 1 L with tap water and adjust to pH 7.0. | |
| Production Medium B | |
| Hydrolysed starch (Dextrin, Corn Products) | 20 g |
| Soya bean flour (Arkasoy 50, British Arkady Co.) | 10 g |
| Distillers solubles (Scotaferm, Thos. Borthwick (Glasgow) Ltd., 60 Wellington Street, Glasgow) | 0.1 g |
| FeSO$_4$.7H$_2$O | 0.1 g |
| Make up to 1 L with deionised water and adjust to pH 7.0 | |
| Seed and Production Medium C | |
| Glyceryl trioleate (Estol 1434, Price's Chemicals Ltd) | 10 g |
| Soya bean flour (Arkasoy 50, British Arkady Co.) | 15 g |
| KH$_2$PO$_4$ | 1.0 g |
| Make up to 1 L with deionised water and adjust to pH 7.0 | |
| Seed and Production Medium D | |
| Soya bean flour (Arkosoy 50, British Arkady Co.) | 22.5 g |
| KH$_2$PO$_4$ | 1.0 g |
| Glyceryl trioleate (Estol 1434, Price's Chemicals Ltd.) | 15.0 g |
| Hydrolysed starch (Dextrin, Corn Products) | 8.0 g |
| Make up to 1 L with deionised water and adjust to pH 7.0 | |

+Trace element solution made up as follows:-
| | |
|---|---|
| FeSO$_4$.7H$_2$O | 0.1 g |
| MnSO$_4$.H$_2$O | 0.1 g |
| ZnSO$_4$.7H$_2$O | 0.1 g |
| Make up to 100 ml with deionised water. | |

*Trace element solution made up as follows:-
| | |
|---|---|
| CaCl$_2$.6H$_2$O | 14.9 g |
| MgCl$_2$.6H$_2$O | 10.0 g |
| NaCl | 10.0 g |
| FeCl$_3$ | 3.0 g |
| ZnCl$_2$ | 0.5 g |
| CaCl$_2$ | 0.39 g |
| MnSO$_4$.H$_2$O | 0.38 g |
| Make up to 1 L with distilled water. | |

EXAMPLE 20

Production of *S. lavuligerus* cells for disruption

A seed flask (50 ml of seed medium A in a 250 ml conical flask) was inoculated with a loopful of spores from a solid medium culture of *S. clavuligerus* and shaken at 240 rpm for 48 hours at 26° C. Aliquots (1 ml) were then aseptically transferred to production flasks (30 ml of production medium A in 250 ml conical flasks) which were shaken at 240 rpm for 48 hours at 26° C. The contents of the flasks were than centrifuged at 15,000×g for 10 minutes at 4° C. The supernatant fluid was discarded and the mycelial pellet resuspended in cold (4° C.) water to their original volume, then centrifuged again at 15,000×g for 10 minutes at 4° C. The supernatant fluid was discarded and the mycelial pellet used for preparing the enzyme as described in the examples below.

EXAMPLE 21

Preparation of crude cell homogenate of *S. clavuligerus* by ultrasonication

The mycelial pellet, prepared as in Example 20, was resuspended in 50 mM tris(hydroxymethyl)aminomethane ('tris') buffer pH 7.0 at a concentration of 1.0 g wet weight per 2.0 ml of buffer. This suspension was divided into 20 ml aliquots and the mycelium was disrupted by ultrasoniction at 25 kHz (MSE Soniprep, Fisons plc, Crawley, Sussex, UK) using 4×10 second bursts with 10 second intervals whilst cooling on an ice/water bath.

EXAMPLE 22

Preparation of crude cell homogenate of *S. clavuligerus* by X-Press disruption

Mycelial pellet (6 g wet weight) prepared as in Example 20, was placed in the cylinder of an X-Press machine (AB Biox, Jarealla, Sweden) which had been cooled to −35° C. The cells were disrupted by forcing them twice through the orifice of the X-Press by applying a pressure of approximately 12 tonnes. The smashed cells were then resuspended in 12 ml of 50 mM tris buffer pH 7.0.

EXAMPLE 23

Preparation of crude cell homogenate of *S. clavuligerus* by grinding with alumina Mycelial pellet (4 g wet weight), prepared as in Example 20, was placed in a mortar, which had been cooled to 4° C., and ground with 1 g of alumina. The disrupted cells were resuspended in 8 ml of 50 mM tris buffer pH 7.0.

EXAMPLE 24

Preparation of a clarified cell-free extract from *S. clavuligerus*

Crude cell homogenate prepared as in Examples 21, 22, 23 or 24 was centrifuged at 38,000×g for 12.5 minutes at 4° C. in order to remove solid cell debris. The clarified supernatant was decanted and used as the cell-free extract.

EXAMPLE 25

Assay of dioxygenase activity

Dioxygenase activity was assayed routinely in 1 ml reactions containing 5 mM 5-amino-3-hydroxy-2-(2-oxoazetidin-1-yl)valerate plus 1 mM ferrous sulphate, 5 mM α-ketoglutarate and the enzyme sample in question. All reagents were made up in 50 mM 3-(N-morpholino)propanesulphonic acid (MOPS) buffer pH 7.0. The reactions were incubated for 10 minutes at 28° C. with agitation and aeration. The reactions were stopped by the addition of an equal volume of ice-cold methanol and centrifugation for 2 minutes at 16,000×g. Aliquots (200 μl) of the supernatants were mixed with 100 μl aliquots of imidazole reagent [206 g imidazole dissolved in 1 liter water; adjusted to pH 6.8 with hydrochloric acid] and left at room temperature for 30 minutes before injecting onto an HPLC column. The hplc conditions were as follows:

Column: μBondapak C$_{18}$ (Millipore Waters, Harrow, Middlesex, UK)

Mobile phase: 0.1M sodium phosphate buffer pH 3.2+6% methanol

Flow rate: 2 ml/minute

Detection wavelength: 313 nm

The reaction was monitored for the production of the imidazole adduct of compound I which has a retention time of 2.1 minutes. The above imidazole precolumn derivatisation HPLC system can also be used to detect clavulanic acid (retention time=5 minutes).

EXAMPLE 26

Production of a sample of partially purified dioxygenase enzyme from *S. clavuligerus*

Mycelial pellet (125 g wet weight) produced as in Example 20 was resuspended in 250 ml of an aqueous solution of 1 mM ethylenediaminetetra-acetic acid at pH 7.0 and ultrasonicated as described in Example 21. The disrupted cell suspension was centrifuged at 21,000×g for 15 minutes and the supernatant decanted. Streptomycin sulphate was added to the supernatant to give a final concentration of 1% w/v. The supernatant was left on ice for 30 minutes and centrifuged at 24,000×g for 20 minutes. The supernatant was then decanted and brought to 50 percent saturation by addition of solid ammonium sulphate. The suspension was left on ice for 1 hour and recentrifuged. The supernatant was brought to 80 percent saturation with solid ammonium sulphate, left on ice for 1 hour and centrifuged at 24,000×g for 60 minutes. The pellet was resuspended in 20 ml of 50 mM tris buffer, pH 7.0, and dialysed overnight against three liters of the same buffer. The dialysed material was then freeze-dried. As a freeze-dried extract the dioxygenase enzyme is stable for several months at −20° C. The specific activity of the enzyme was 0.0173 units/mg protein. One unit is the amount of enzyme which will produce 1 μmole of compound I from compound II per minute at 28° C. and at pH 7.0.

Dioxygenase activity was assayed using the method described in Example 25.

EXAMPLE 27

Preparation of a substantially purified sample of dioxygenase enzyme from *S. clavuligerus*

Freeze-dried partially purified enzyme (250 mg) prepared as described in Example 26 was loaded onto a DEAE Sepharose CL-6B (Pharmacia, Uppsala, Sweden) column (30×2.4 cm), washed with 100 ml of 50 mM tris buffer pH 7.0 and eluted with a gradient of 50 to 500 mM tris buffer pH 7.0. Dioxygenase positive fractions were pooled and brought to 80% saturation with solid ammonium sulphate. The suspension was kept on ice for 1 hour and centrifuged at 24,000×g for 60 minutes. The precipitate was resuspended in 1 ml of 50 mM tris buffer pH 7.0 plus 0.5 ml 30 % sucrose solution (made up in the same buffer) and loaded onto a Sephadex G75 superfine (Pharmacia) column (63.5×3.5 cm) which was eluted with 50 mM tris buffer. Dioxygenase positive fractions were pooled, brought to 80 percent saturation with solid ammonium sulphate and the resulting precipitate was removed by centrifugation and stored at 20° C. At this stage the dioxygenase enzyme produced a single band corresponding to a molecular weight of approximately 8,000 daltons when examined by sodium dodecyl sulphate polyacrylamide gel electrophoresis. The isoelectric point was determined by isoelectric focusing and gave a value of pI=5.65.

Dioxygenase activity was measured using the method described in Example 25.

EXAMPLE 28

Isolation of 5-amino-3-hydroxy-2-(2-oxo-azetidin-1-yl)-valeric acid (Compound II) from *Streptomyces clavuligerus*

A 300 L fermentation vessel, fitted with an 8½ inch disc impeller, containing 150 L of production medium A (as given in Example 19) was inoculated with 1.5 L of a culture of *Steptomyces clavuligerus* which had been grown for 48 hours in seed medium A (as given in Example 19). The vessel was stirred at 570 rpm and sparged with 150 L sterile air per minute. Foaming was controlled by the presence of 0.02 % Pluronic L81 (Blagden-Campbell Chemical Co., Croydon, UK.) antifoam in the medium. The vessel was maintained at 26° C. for 48 hours. The culture was then chilled to 5° C. and the cells removed by continuous centrifugation. The cell paste was resuspended in 75 liters of water at 1°–5° C. and the cells disrupted by passing through a Manton-Gaulin homogeniser (Model 15M-8BA, APV, Crawley, Sussex, UK) at a pressure of 3000–5000 psi. The cell debris was removed by continuous centrifugation and the supernatant was ultrafiltered using an Alfa Laval UFS-4 ultrafiltration rig containing 10 sq meters of PM1 polysulphone membrane with a nominal molecular weight cut-off value of 10,000 daltons. The low-moleular weight fraction was concentrated by reverse osmosis to a volume of 6L which was freeze dried to yield 474 g of solids (Batch 1) containing compound II (Compound II was assayed by conversion to compound I using a dioxygenase preparation then monitoring the amount of compound I formed using the precolumn imidazole derivatisation hplc method desribed in Example 25. As the conversion of compound II to compound I was not always quantitative the assay was used as a qualitative guide for the selection of fractions containing compound II). A second fermentation and isolation were performed in identical manner to yield 544 g of freeze-dried solids (Batch 2) containing compound II.

A portion of the freeze-dried solids (166 g of Batch I plus 334 g of Batch 2) was further purified in 5×100 g aliquots as follows. Each 100 g aliquot was dissolved in 140 ml of water, 140 ml of ethanol was then added and the suspension spun at 10,000g for 15 minutes. The precipitate was discarded and the supernatant containing compound II chromatographed on a silica 60 230–400 mesh (E. Merck, Damstadt, W. Germany) column 18×19.5 cm packed in industrial methylated spirit (IMS) and eluted with 85% IMS/15 % water at 45 ml/min. The fractions containing compound II from all five runs were bulked and rotary evaporated to dryness to give 66.5 g of solids. This weight was reduced to 25 g by reprocessing the material on a similar size silica 60 column as above. The sample was then chromatographed twice on a Diaion HP20 SS (Mitsubishi Chemical Industries Ltd., Tokyo, Japan.) column, 8×50 cm packed in water and eluted with water at 7 ml/min. Fractions containing compound II were pooled, rotary evaporated to dryness (10.0 g) redissolved in 34 ml water and loaded onto a Biogel P2 column (Bio-Rad Laboratories, Watford, Hertfordshire, UK) 8×57.5 cm packed in water. The compound was eluted with water at 5 ml/min. Fractions containing Compound II were bulked and rotary evaporated to give 5.25 g solids.

These were dissolved in 6 ml water, 6 ml of ethanol was then added and the solution loaded onto a Merck silica 60 (230–400 mesh) column 5×21 cm packed in 85% ethanol/15% water at 2 ml/min. Positive fractions were then recycled through a similar column prior to further purification of the sample (2.15 g) by Biogel P2 column chromtography, 2.7×117 cm packed in water and eluted with water at 0.8 ml/min. Eluate fractions containing compound II were bulked and rotary evaporated to dryness to give 580 mg of sample of 60–70% purity as judged by nmr spectroscopy.

A small portion of this sample was purified to homogeneity by high pressure liquid chromatography using a reverse-phase system (Millipore Waters μ-Bondapak CN column, 3.9 mm×30 cm, eluted with water at 0.7 ml/min). The sample (21.85 mg) was dissolved in water at 10 mg/ml and injected onto the column in 15 μl aliquots. The major peak (UV detection at 205 nm) was collected as one discrete fraction, concentrated then rechromatographed as above then rotary evaporated to give 7.3 mg of compound II as a colourless glassy solid. $v_{max}$ (KBr) 3400, 2900, 1720 and 1600 cm$^{-1}$. $\delta_H$ (D$_2$O, 250 MHz), 1.89 (2H, m), 3.02 (2H, t), 3.18 (2H, dt), 3.52 (1H, m), 3.60 (1H, m), 4.08 (1H, d), and 4.22 (1H, m). [Found: MH+(p.i. F.A.B.), 203.1028. [C$_8$H$_{14}$N$_2$O$_4$]H+ requires 203.1032].

EXAMPLE 29

The Conversion of 5-amino-3-hydroxy-2(2-oxoazetidin-1-yl)valeric acid (Compound II) to Z-(2S,5S)-3-(β-aminoethylidene)-7-oxo-4-oxa-1-azabicyclo[3.2.0]-heptane-2-carboxylic acid (Compound I) by cell-free extracts of Streptomyces species A cell-free extract of *S. lipmanii* NRRL 3584 was prepared as described for *S. clavuligerus* in Example 21. A reaction was set up containing 500 μl of the extract, 200 μl of 50 mM 3-(N-morpholino)propanesulphonic acid buffer pH 7.0, 100 μl of 10 mM α-ketoglutarate (made up in the same buffer), 100 μl of 10 mM FeSO$_4$ (made up in H$_2$O) and 100 μl of 10 mg/ml compound II (prepared as in Example 13 but without separation of diastereoisomers). The reaction was incubated for 60 minutes at 28° with aeration and agitation. After 60 minutes the imidazole precolumn imidazole derivatisation hplc assay (described in Example 25) indicated that cyclisation of compound II to compound I had occurred. Cell-free enzyme extracts were also prepared from *S. jumonjinensis* ATCC 29864 and *S. katsurahamanus* T-272 as described for *S. clavuligerus* in Example 21. Each extract was incubated with 1 mM α-ketoglutarate and 1 mM ferrous sulphate at 28° C. in 50 mM MOPS buffer. The reaction mixtures were examined by hplc, when it was found that the endogenous compound II in the extracts had been converted to compound I over a 1 hour period.

EXAMPLE 30

The conversion of
5-amino-3-hydroxy-2-(2-oxoazetidin-1-yl)valeric acid (compound II) to
Z-(2S,5S)-3-(β-aminoethylidene)-7-oxo-4-oxa-1-azabicyclo[3.2.0]heptane-2-carboxylic acid (compound I) by a partially purified dioxygenase preparation from *Streptomyces clavuligerus*

A reaction mixture was set up containing 15 mg/ml of a freeze-dried dioxygenase preparation (prepared as described in Example 26), 1 mM ferrous sulphate, 5 mM α-ketoglutarate, 5 mM compound II (one diastereoisomer, prepared as in Example 14) and 50 mM 3-(N-morpholino) propanesulphonic acid at pH 7.0. The reaction mixture was continuously shaken (to ensure adequate transfer of atmospheric oxygen) at 28° C. After 60 minutes the reaction mixture was examined by the precolumn imidazole derivatisation method described in Example 25 when it was found that 42% of compound II (i.e. 84% of the enantiomer with the natural stereochemistry) had been converted to compound I.

EXAMPLE 31

A large-scale enzymatic conversion of
5-amino-3-hydroxy-2-(2-oxoazetidin-1-yl)valeric acid (compound II) to
Z-(2S,5S)-3-(β-aminoethylidene)-7-oxo-4-oxa-1-azabicyclo[3.2.0]heptane-2-carboxylic acid (compound I) and subsequent isolation by derivatisation In the following experiment the fact that compound II and the dioxygenase enzyme both occur in *Streptomyces clavuligerus* was exploited by disrupting *S. clavuligerus* cells and allowing the endogenous enzyme to convert the endogenous compound II to give compound I. The methods for producing the smashed cells were essentiall the same as given in Example 28.

150 liters of a 48 hour *Streptomyces clavuligerus* culture was centrifuged and the mycelium was resuspended to 90 liters in H₂O at 5° C. The cells were then disrupted using a Manton-Gaulin homogeniser operating at 3,000–5,000 psi. α-Ketoglutarate and ferrous sulphate were both added to the smashed cell suspension to give final concentrations of 1 mM; the concentration of compound II in the mixture was 16 μg/ml. The mixture was stirred and sparged with air for 30 minutes at pH 7.0 at 25° C. Cell debris was then removed by centrifugation, and the supernatant, containing compound I, was ultrafiltered. The filtrate was concentrated to 6.2 liters (containing approx. 600 mg of compound I) by reverse osmosis. Compound I was then converted to the N⁵-benzyloxycarbonyl (CBZ) derivative as follows.

6.2 Liters of acetone was added to the concentrate followed by addition of 600 ml of 50% benzylchloroformate in acetone, over a 10 minute period, maintaining pH 7.5–8.0 (5° C.). The reaction was kept at pH 7.5 for a further 30 minutes then returned to pH 7.0. The acetone was removed by rotary evaporation, to give 4.75 liters of concentrate.

The solution was extracted with ½ volume and ¼ volume ethyl acetate at pH 2.0, 5° C. The extracts were bulked and back extracted into water at pH 7.0, using ½ and ¼ of the ethyl acetate volume.

The bulked back extracts were made up to 5 liters with H₂O and adsorbed onto an IRA anion exchange column (acetate cycle, 22×5 cm, flow rate 25 ml/min) and desorbed with 1 M NaCl. The product was desalted by the above ethyl acetate extraction procedure. Aqueous back-extraction followed by freeze-drying gave the crude CBZ derivative of I. A portion of this product was converted to the benzyl ester as follows.

100 g freeze-dried derivative was dissolved in 120 ml dimethylformamide, and 60 ml benzyl bromide added. The reaction was stirred for 7 hours at room temperature and left overnight at 5° C. 1 liter of ethyl acetate (5° C.) was then added, and the resultant precipitate removed by centrifugation. The supernatant was rotary evaporated to 300 ml, and washed with 4 M NaCl (200 ml, then 100 ml) at pH 7.0. Further rotary evaporation gave a syrup (100 ml) which was washed with cyclohexane (200 ml). The syrup was loaded onto a silica column (Merck silica Art. 7734), 9.5×17 cm, and eluted with a petroleum ether/ethyl acetate gradient of 6:1 to 1:1.

The product was identified by silica tlc, petroleum ether/ethyl acetate(2:1); Rf 0.4, detected as a red spot using the triphenyltetrazolium spray reagent described in Example 33. Positive fractions were bulked and rotary evaporated, giving 3.9 g of oil.

This was loaded onto a silica column (Silica 'S', 230–400 mesh,Reidel-de Haën AG, Seelze, W. Germany), 5×14 cm, flow rate 8 ml/min and eluted with a 2 to 5% ethanol in chloroform gradient. Positive fractions were rotary evaporated to give 590 mg of gum (approx. 20% pure). This product was loaded onto a Sephadex LH 20 (Pharmacia, Uppsala, Sweden) column, 18×3 cm, flow rate 2 ml/min, eluting with chloroform/cyclohexane(1:1) to give 230 mg (approx. 30% pure) which was further purified in a silica column (silica 'S', 230–400 mesh, 19×3.5 cm, flow rate 3 ml.min), eluted with 5% ethyl acetate in chloroform. The resulting material was a substantially pure sample of the N⁵-CBZ benzyl ester of compound I (63 mg).

$\nu_{max}$ (KBr) 3300, 1800, 1730, and 1690 cm⁻¹. $\delta_H$ (CDCl₃, 90 MHz) 2.98 (1H, d, J 16 Hz), 3.42 (1H, dd, J 16 and 3 Hz), 3.81 (2H, t, J 7 Hz), 4.68 (2H, m), 5.0 (1H, s), 5.07 (2H, s), 5.14 (2H, s), 5.61 (1H, d, J 3 Hz) 7.30 (10H, s). $\delta_C$(CDCl₃, 63 MHz) 36.66 (C-6), 46.33 (C-10), 60.47 (C-2), 66.71 (Ar-CH₂), 67.77 (Ar-CH₂), 87.93 (C-5), 97.51 (C-9), 128.12 (Aryl-C) 128.40 (Aryl-C), 136.51 (Aryl-C), 152.51 (C-3), 156.14 (CH₂NHCO) 166.87 (C-8), 174.42 (C-7). [MH⁺ (F.A.B.) 423.1561; (C₂₃H₂₄N₂O₆)H⁺ requires 423.1556].

The N⁵-CBZ benzyl ester of compound I gave a negative Cotton effect with a minimum at 243 nm in the CD spectrum.

A 50 mg portion of this material was deprotected as follows. The sample was dissolved in 15 ml ethyl acetate/ethanol (70:30) and added to 50 mg 10% palladium on carbon catalyst. The mixture was hydrogenated at one a atmosphere pressure for 15 minutes. Tlc examination indicted incomplete deprotection (silica Merck Art. 5719, ethanol/water, 90:10, Rf 0.2). The catalyst was removed by filtration and retained, and the hydrogenation was repeated with fresh catalyst. On completion of the reaction the first batch of catalyst was added to the reaction mixture, and the suspension rotary evaporated to dryness. Water (20 ml) was added to dissolve the product, and the catalyst removed by centrifugation. The aqueous product was concentrated to 1.5 ml. This was loaded a onto Diaion HP20 SS column (1.5×20 cm, flow rate 1.5 ml/min) and eluted with water Positive fractions were identified by tlc, then bulked and freeze-dried to give 5.7 mg of compound I. $\nu_{max}$ (KBr) 3430, 1780 and 1640 cm⁻¹. $\delta_H$ (D₂O, 250

MHz) 3.15 (1H, d, J 17 Hz), 3.57 (1H, dd, J 17 and 2.6 Hz), 3.67 (2H, t, J 7.5 Hz), 4.84 (1H, dt, J 7.5 and 1Hz), 5.01 (1H, 1 d, J 1Hz) 5.77 (1H, d, J 2.6 Hz).

EXAMPLE 32

The enzymatic conversion of 3-hydroxy-5-amino-2-(2-oxo[2-$^{13}$C]azetidin-1-yl)[1,2-$^{13}$C$_2$]valeric acid ([$^{13}$C$_3$]-compound II) to [2,7,8-$^{13}$C$_3$]-Z-(2S,5S)-3-($\beta$-aminoethylidene)-7-oxo-4-oxa-1-azabicyclo[3.2.0]heptane-2-carboxylic acid ([$^{13}$C$_3$]-compound I)

[$^{13}$C$_3$]-Compound II (116.4 mg; prepared as in Example 18) was added to a reaction mixture consisting of 1.74 g of freeze-dried dioxygenase enzyme (prepared as in Example 26) dissolved in 97.5 ml of 3-(N-morpholino)propanesulphonic acid buffer pH 7.0 to which was added 2.33 ml of 50mM ferrous sulphate solution and 11.64 ml of 50mM α-ketoglutarate solution. The reaction was incubated at 28° C. in a 500 ml conical flask with continual shaking to ensure adequate transfer of atmospheric oxygen. After 70 minutes the precolumn imidazole derivatisation hplc assay (given in Example 26) indicated that 55.2 mg of compound I had been produced (95% conversion of the biologically active enantiomer). The [$^{13}$C$_3$]-compound I was separated from the inactive enantiomer of [$^{13}$C]-compound II by the following method.

The reaction volume was reduced to 17 ml by rotary evaporation and deproteinated by Biogel P2 (Bio-Rad Laboratories) column chromatography as follows. The sample was loaded onto a column of Biogel P2 (5.2×13.5 cm, packed in water) and eluted at 4° C. with water at 1 ml/min. Fractions containing compound I were pooled, rotary evaporated to dryness, dissolved in 5 ml of water and chromatographed at 4° C. on a Merck silica 60 column (3×16 cm packed in 85% ethanol 15% water) and eluted with the same solvent at 0.6 ml/min. Fractions containing compound I but not compound II were bulked and evaporated to dryness. $^{13}$C nmr analysis of the sample indicated that essentially the only [$^{13}$C$_3$]- labelled species present was [$^{13}$C$_3$]-compound I. A small amount of [$^{13}$C$_3$]-compound II could still be detected, but the quantity of the active enantiomer of [$^{13}$C$_3$]-compound II present would only have amounted to 0.5% of the total labelled species. Analysis of this product by the precolumn imidazole derivatisation hplc method indicated that it contained 18.5 mg of compound I.

The following hplc method was used to detect the presence of compound II in column fractions:
Column: C$_{18}$μ Bondapak (Millipore Waters)
Solvent: 0.1M Sodium phosphate buffer pH 3.0
Flow rate: 1.5 ml/min
Detecting wavelength: 205 nm
Under these conditions compound II has a retention time of 2.55 minutes.

EXAMPLE 33

The conversion of [2,7,8-$^{13}$C$_3$]-Z-(2S, 5S)-3-($\beta$-amino ethylidene)-7-oxo-4-oxa-1-azabicyclo[3.2.0]heptane-2-carboxylic acid ([$^{13}$C$_3$)]-compound I) to [2, 7, 8-$^{13}$C$_3$]-clavulanic acid by growing cells of *Streptomyces clavuligerus*

A 250 ml conical flask containing 30 ml of medium D (Example 19) was inoculated with a loopful of spores of *S. clavuligerus*. The flask was shaken at 26° C. for 65 hours then 1 ml aliquots were transferred to 3 further flasks each containing 30 ml of medium D. After 31 hours shaking at 26° C. the titre of clavulanic acid had reached 129 μg/ml and 6.2 mg of [$^{13}$C$_3$]-compound I was added to each flask. After a further 16.5 hours growth the cultures were harvested by centrifugation and the supernatant freeze-dried. The clavulanic acid titre of the supernatant was 354 μg/ml as measured by the precolumn imidazole derivatisation method given in Example 25.

The freeze-dried solids were slurried with dimethylformamide (15 ml) containing benzyl bromide (0.8 ml) and left at ambient temperature (ca. 20° C.) for 6.5 hours. The resulting benzyl clavulanate was extracted into ethyl acetate and rotary evaporated to give a brown oil. This was loaded onto a silica (Silica 'S' 230–400 mesh, Riedel-de Haën) column (1.5 cm×8.5 cm) packed in cyclohexane/ethyl acetate (6:1) and eluted with a gradient of cyclohexane/ethyl acetate (6:1 to 1:1). Fractions were monitored for the presence of benzyl clavulanate by silica tlc (Merck Art.5719) developed in ethyl acetate/cyclohexane (2:1) and visualised (red spot at Rf ca.0.6) with triphenyltetrazolium chloride spray reagent (4% triphenyltetrazolium chloride in methanol diluted with an equal volume of 1M aqueous sodium hydroxide). Fractions containing benzyl clavulanate were bulked, and rotary evaporated to give a gum. This was loaded onto a Sephadex LH20 (Pharmacia) column (1.5×10 cm) packed in cyclohexane/chloroform (1:1) and eluted with the same solvent. Fractions containing benzyl clavulanate were bulked and evaporated to a coloureess gum (14.2 mg) which was examined by [$^{13}$C]-nmr (100 MHz) and atom % enrichments of [$^{13}$C] were calculated with reference to a natural abundance spectrum. Significant enrichments were detected at carbons 2, 7 and 8 only, and the incorporation of each [$^{13}$C]-label into clavulanic acid was equal to approx. 4.3 %. Long range $^{13}$C-$^{13}$C spin-spin couplings were detected due to concomitant enrichment of carbons 7, 2 and 8 indicating that the bonds between carbons 7, 2 and 8 had remained intact during incorporation.

$^1$H nmr analysis was carried out on the labelled benzyl clavulanate to ensure that the label was in clavulanic acid rather than due to contamination by [$^{13}$C$_3$]-compound I or a derivative thereof. The 400 MHz $^1$H nmr spectrum showed no signals that could be attributed to the presence of a 10-aminodeoxyclavulanate species. In order to be doubly certain of this point the sample of [$^{13}$C$_3$]-benzyl clavulanate was converted to the 10-methyl ether by the following method: [2, 7, 8$^{13}$C$_3$]-Benzyl clavulanate (8.5 mg, 29 mmol) was dissolved in dichloromethane (3.5 ml) and treated with magnesium sulphate (30 mg, 250 μmol, dried at 170° C. for 24 hrs) and silver (I) oxide (23 mg, 100 μmol dried at 170° C. for 3.5 hours). The resulting suspension was stirred for three days with methyl iodide (0.2 ml, 3.2 mmol) at room temperature and in the dark.

The reaction mixture was evaporated to dryness and chromatographed over silica gel (Merck Art. 9385) in ethyl acetate/hexane (1:2) to provide benzyl 10-O-methylclavulanate as an oil (4.2 mg, 47%); $\nu_{max}$ (KBr) 1804, 1751, 1695, 743, and 699 cm$^{-1}$; $\delta_H$ (CDCl$_3$; 250 MHz) 3.08 (1 H, dd, J 16.7 and 0.5 Hz), 3.28 (3H, s), 3.49 (1 H, dd, J 2.8 and 16.8 Hz), 4.00 Hz (2H, m), 4.82 (1H, dt, J 7.1 and 1.3 Hz), 5.10 (1H, d, 0.9 Hz), 5.20 (2H, s), 5.70 (1H, dd, J 2.7 and 0.5 Hz) and 7.37 (5H, m); $\delta_C$ (CDCl$_3$; 100 MHz) 46.39, 57.74, 60.60 (dd, J 67.4 and 2.0 Hz), 60.61, 66.36, 67.85, 87.89, 97.66, 128.67, 134.70, 153.11, 166.91, (dd, J 67.5 and 3.5 Hz), 166.87, and 174.25 (m); (Found ++NH₄, 321. $C_{16}H_{17}NO_5+NH_4^+$ requires 321).

Samples of the methyl ether of benzyl [$^{13}C_3$] clavulanate and of the methyl ether of unlabelled benzyl clavulanate were found to have the same retention time (19.5 minutes) when examined by gas chromatography. (Column: 25 metre BPI capillary; carrier gas: helium; temperature programme: 2 minutes at 120° C., then increased by 8° C./minute to 280° C.). Peaks eluting at the retention time of the methyl ether of benzyl clavulanate were examined by mass spectrometry. Data for repeat scans were accumulated and averaged by computer. Comparison of the mass spectra for the labelled and unlabelled samples showed that the labelled material contained 4% triple [$^{13}C$]-labelled species. Thus it was confirmed that [2, 7, 8-$^{13}C_3$]- compound I was converted to [2,7,8-$^{13}C_3$]-clavulanic acid by growing cells of S. clavuligerus.

EXAMPLE 34

The conversion of Z-(2S, 5S)-3-(β-amino ethylidene)-7-oxo-4-oxa-1-azabicyclo[3.2.0]-heptane-2-carboxylic acid (Compound I) to clavulanic acid by partially purified enzyme extract of S. clavuligerus A clarified cell-free extract of S. clavuligerus was prepared as in Examples 21 and 24. Streptomycin sulphate (1% w/v) was added at 0° C. and left for 1 hour. The suspension was centrifuged at 35,000×g for 30 min at 4° C., and the supernatant retained. Ammonium sulphate was added to give a concentration of 80% saturation and the suspension left for 18 hours at 4° C. The suspension was centrifuged at 35,000×g for 1 hour at 4° C. The supernatant was discarded and the pellet resuspended in 50 mM 'tris' buffer pH 7.0. The solution was dialysed (Visking memorane, size 1, Medicell International) for 2×1 hour periods in the above buffer, and then freeze-dried to give the partially purified enzyme extract as a powder.

A reaction was set up containing the above enzyme extract (40 mg/ml), compound I (1 mM), sodium pyruvate (1 mM), pyridoxal-5-phosphate (1 mM), β-nicotinamide dinucleotide phosphate (reduced form; 1 mM) all dissolved in 50 mM 3-(N-morpholino)propanesulphonic acid, pH 7.0. The reaction mixture was incubated at 28° C. for 1 hour. During this period the clavulanic acid titre rose from less than 0.1 μg/ml to 0.6 μg/ml. The above reaction was repeated substituting sodium glyoxylate or α-ketobutyrate for sodium pyruvate. On both occasions the titre of clavulanic acid rose from less than 0.1 μg/ml to 0.8 μg/ml. Clavulanic acid titres were measured using the precolumn imidazole derivatisation HPLC method described in Example 25.

We claim:

1. A compound of the formula (I) or a salt or protected form thereof:

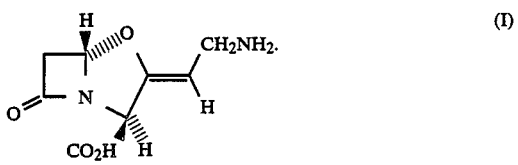

2. A compound according to claim 1 selected from the following:
   Z-(2S,5S)-3-(β-aminoethylidene)-7-oxo-4-oxa-1-azabicyclo[3.2.0]heptane-2-carboxylic acid;
   Z-(2S,5S)-3-(β-benzyloxycarbonylaminoethylidene)-7-oxo-4-oxa-1-azabicyclo[3.2.0]heptane-2-carboxylic acid; and
   benzyl Z-(2S,5S)-3-(β-benzyloxycarbonylaminoethylidene)-7-oxo-4-oxa-1-azabicyclo[3.2.0.]heptane-2-carboxylate.

* * * * *